United States Patent
Fritzsche et al.

(10) Patent No.: US 12,054,842 B2
(45) Date of Patent: Aug. 6, 2024

(54) COMPOSITION FOR TIN-SILVER ALLOY ELECTROPLATING COMPRISING A COMPLEXING AGENT

(71) Applicant: BASF SE, Ludwigshafen am Rhein (DE)

(72) Inventors: Katharina Fritzsche, Weil am Rhein (DE); Doris Kremzow-Graw, Ludwigshafen (DE); Marco Arnold, Ludwigshafen (DE); Alexander Fluegel, Ludwigshafen (DE)

(73) Assignee: BASF SE, Ludwigshafen Am Rhein (DE)

( * ) Notice: Subject to any disclaimer, the term of this patent is extended or adjusted under 35 U.S.C. 154(b) by 923 days.

(21) Appl. No.: 17/040,642

(22) PCT Filed: Mar. 22, 2019

(86) PCT No.: PCT/EP2019/057205
§ 371 (c)(1),
(2) Date: Sep. 23, 2020

(87) PCT Pub. No.: WO2019/185468
PCT Pub. Date: Oct. 3, 2019

(65) Prior Publication Data
US 2021/0025070 A1 Jan. 28, 2021

(30) Foreign Application Priority Data

Mar. 29, 2018 (EP) .................................... 18165026

(51) Int. Cl.
*C25D 3/32* (2006.01)
*B32B 33/00* (2006.01)
(Continued)

(52) U.S. Cl.
CPC ................ *C25D 3/32* (2013.01); *B32B 33/00* (2013.01); *C07D 213/32* (2013.01); *C25D 3/46* (2013.01);
(Continued)

(58) Field of Classification Search
CPC ... C25D 3/32; C25D 3/46; C25D 3/60; C25D 5/02; C25D 3/64; B32B 33/00; C07D 213/32
See application file for complete search history.

(56) References Cited

U.S. PATENT DOCUMENTS 4,871,429 A 10/1989 Nobel et al.
5,011,763 A * 4/1991 Morimoto .......... G03C 7/39228
430/460

(Continued)

FOREIGN PATENT DOCUMENTS

CN 102597329 A 7/2012
EP 0 144 990 A2 6/1985
(Continued)

OTHER PUBLICATIONS

Kaptein et al., Journal of Organic Chemistry, vol. 55, issue 6, pp. 1890-1901 (Year: 1990).*
Adhikary et al., Inorganic Chemistry, vol. 32, issue 26, pp. 5957-5962, 1993 (Year: 1993).*
Adhikary et al., Inorganica Chemica Acta, vol. 261, issue 1, pp. 15-21 (Year: 1997).*
Gilbert et al., Journal of Hetrocyclic Chemistry, vol. 39, issue 2, pp. 399-404. (Year: 2002).*
Hochreuther et al., Inorganic Chemistry, vol. 50, issue 24, pp. 12747-12761 (Year: 2011).*
Kirk, Protein Expression and Purification, vol. 95, pp. 1-7 (Year: 2014).*
Donkuru et al. Journal of Chromatography A, vol. 1446, pp. 114-124 (Year: 2016).*

(Continued)

*Primary Examiner* — Yate' K Cutliff
(74) *Attorney, Agent, or Firm* — Armstrong Teasdale LLP

(57) ABSTRACT

An aqueous composition comprising (a) metal ions comprising tin ions and silver ions and (b) at least one complexing agent of formula (C1) $R^1—X^1—S—X^{21}[D^1-X^{22}—]_n—S—X^3—R^2$, (C2) $R^1—X^1—S—X^{31}-D^2-[X^{32}—S—]_nX^3—R^2$, (C3) $R^3—X^1—S—X^{41}-[D^3-X^{42}—]_nS—X^3—R^4$ wherein $X^1$, $X^3$ are independently selected from a linear or branched $C_1$-$C_{12}$ alkanediyl, which may be unsubstituted or substituted by OH; $X^{21}$, $X^{22}$ are independently selected from $X^1$, which may be further substituted by $—X^5—COOR^{12}$, $—X^5—SO_2—O—R^{12}$, a $C_2$ to $C_6$ polyoxyalkylene group of formula $—(O—CH_2—CHR^{11})_z—OH$, or a combination thereof, and $—X^1—NH—CO—X^6—CO—NH—X^1—$; $X^{31}$, $X^{32}$ are independently selected from a chemical bond and $X^1$; $X^{41}$, $X^{42}$ are independently selected from $X^1$; $X^5$ is a linear or branched Ci to C10 alkyl; $X^6$ is selected from $X^1$ and a divalent 5 or 6 membered aromatic group; $R^1$, $R^2$ are independently selected from a monovalent 5 or 6 membered aromatic N-heterocyclic group comprising one N atom or two N atoms which are separated by at least one C atom, and its derivatives received by N-alkylation with a $C_1$-$C_6$-alkyl group, which may be substituted by $—COOR^{12}$ or $—SO_2—O—R^{12}$, and which aromatic N-heterocyclic group may optionally further comprise, under the proviso that X21 is substituted by at least one OH, one S atom; $R^3$, $R^4$ are independently selected from a monovalent 5 or 6 membered aliphatic N-heterocyclic group comprising one N atom and one O atom; $D^1$ is independently selected from S, O and $NR^{10-}$; $D^2$ is (a) a divalent 5 or 6 membered aliphatic heterocyclic ring system comprising 1 or 2 S atoms, or (b) a 5 or 6 membered aromatic heterocyclic ring system comprising at least two N atoms and optionally one or two S atoms; $D^3$ is independently selected from S and $NR^{10-}$; n is an integer of from 0 to 5; z is an integer from 1 to 50; $R^{10}$ is selected from H and a linear or branched $C_1$-$C_{12}$ alkyl; $R^{11}$ is selected from H and a linear or branched $C_1$ to $C_6$ alkyl; and $R^{12}$ is selected from R10 and a cation.

19 Claims, No Drawings

(51) Int. Cl.
  *C07D 213/32* (2006.01)
  *C25D 3/46* (2006.01)
  *C25D 3/60* (2006.01)
  *C25D 3/64* (2006.01)
  *C25D 5/02* (2006.01)
  *C25D 7/00* (2006.01)

(52) U.S. Cl.
  CPC ............... *C25D 3/60* (2013.01); *C25D 3/64* (2013.01); *C25D 5/02* (2013.01); *C25D 7/00* (2013.01)

(56) References Cited

U.S. PATENT DOCUMENTS

| | | | |
|---|---|---|---|
| 5,174,887 | A | 12/1992 | Federman et al. |
| 6,607,653 | B1 | 8/2003 | Tsuji et al. |
| 7,628,903 | B1 | 12/2009 | Tsuji et al. |
| 7,781,325 | B2 | 8/2010 | Lee et al. |
| 8,980,077 | B2 | 3/2015 | Romer et al. |
| 9,869,029 | B2 | 1/2018 | Roeger-Goepfert et al. |
| 10,612,150 | B2 | 4/2020 | Tatsumi et al. |
| 2006/0094226 | A1 | 5/2006 | Huang et al. |
| 2008/0054459 | A1 | 3/2008 | Lee et al. |
| 2008/0296761 | A1 | 12/2008 | Lee et al. |
| 2013/0334052 | A1 | 12/2013 | Chua et al. |
| 2017/0137960 | A1 | 5/2017 | Chua et al. |
| 2018/0371637 | A1 | 12/2018 | Chua et al. |
| 2019/0368063 | A1 | 12/2019 | Yamaguchi et al. |

FOREIGN PATENT DOCUMENTS

| | | |
|---|---|---|
| EP | 0 166 347 A2 | 1/1986 |
| EP | 0 854 206 A1 | 7/1998 |
| JP | 2006183079 A | 7/2006 |
| JP | 2006-206946 A | 8/2006 |
| JP | 2007-218952 A | 8/2007 |
| JP | 4296358 B2 | 7/2009 |
| JP | 2017119911 A | 7/2017 |
| WO | WO 2010/069810 A1 | 6/2010 |
| WO | WO 2016/020216 A1 | 2/2016 |
| WO | WO 2017/121657 A1 | 7/2017 |
| WO | 2017217387 A1 | 12/2017 |
| WO | WO 2018/219848 A1 | 12/2018 |

OTHER PUBLICATIONS

Binz et al., Journal of the American Chemical Society, vol. 61, issue 11, pp. 3134-3139. (Year: 1939).*
Grogan et al., Journal of Organic Chemistry, vol. 20, issue 1, pp. 50-59 (Year: 1955).*
Salas-Coronado et al., Journal of Molecular Structure, vol. 640, pp. 95-108 (Year: 2003).*
Khirullina et al., Russian Journal of Organic Chemistry, vol. 49, No. 7, pp. 902-907 (Year: 2012).*
International Search Report issued on Apr. 25, 2019 in PCT/EP2019/057205 filed on Mar. 22, 2019.
Extended European Search Report issued Oct. 12, 2018 in European Patent Application No. 18165026.8, 3 pages.

* cited by examiner

COMPOSITION FOR TIN-SILVER ALLOY ELECTROPLATING COMPRISING A COMPLEXING AGENT

BACKGROUND OF THE INVENTION

The invention relates to tin-silver alloy electroplating compositions comprising a complexing agent, their use and processes for tin-silver alloy electroplating.

Metals and metal-alloys are commercially important, particularly in the electronics industry where they are often used as electrical contacts, final finishes and solders.

Leadfree solders, such as tin, tin-silver, tin-copper, tin-bismuth, tin-silver-copper, and others, are common metals used in solders. These solders are often deposited on semiconductor substrates by means of metal electroplating plating baths.

Certain applications for lead-free solder plating present challenges in the electronics industry. For example, when used as a capping layer on copper pillars, a relatively small amount of lead-free solder, such as tin or tin-silver solder, is deposited on top of a copper pillar.

A typical tin-silver plating solution comprises dissolved tin and silver ions, water, an acid electrolyte such as methane sulfonic acid in an amount sufficient to impart conductivity to the bath, an antioxidant, and proprietary additives to improve the uniformity of the plating and the quality of the metal deposit in terms of surface roughness and void formation. Such additives usually include complexing agents that are capable of forming a complex with silver in order to allow silver to be (a) stable in the solution in combination with tin, and (b) deposited in parallel to the less noble tin.

JP 2007218952 A, EP 166347 A, EP 144990 A disclose photographic films which comprise silver compounds and a sulfur containing compound comprising nitrogen containing ring system substituents like 1,8-Bis(2-pyridyl)-3,6-dithiaoctane or 1,11-Bis(2-pyridyl)-3,6,9-trithiaundecane.

JP 2006206946 A discloses silver plating bath comprising, among others, compounds of formula $R_a$—S—$(CH_2$—$CH_2$—S$)_n$—$R_b$. The bath may be used for depositing silver on printed circuit boards, semiconductor integrated circuits, resistors, variable resistors, capacitors, filters, inductors, thermistors, crystal oscillators, switches, wire and other electronic components.

U.S. Pat. No. 6,607,653 B1 discloses a composition for depositing a tin copper, a tin copper bismuth, or a tin copper silver alloy that comprises a specific sulfur containing compound. One of several dozens of compounds could be 1,10-di(2-pyridyl)-1,4,7,10-tetrathiadecane.

Surprisingly it was found that the compounds mentioned above may advantageously be used in electroplating baths to deposit tin-silver alloys.

It is an object of the present invention to provide a tin-silver electroplating composition that is stable over a long time without showing significant deterioration or aging, e.g. by strong coloring or generating deposits and that is capable of electrodepositing tin-silver alloys on semiconductor substrates.

SUMMARY OF THE INVENTION

The present invention provides an aqueous composition comprising (a) metal ions comprising tin ions and silver ions and (b) at least one complexing agent of formula C1, C2 or C3

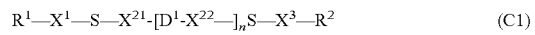  (C1)

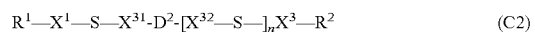  (C2)

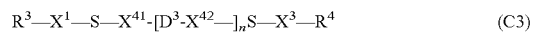  (C3)

wherein
$X^1$, $X^3$ are independently selected from a linear or branched $C_1$-$C_{12}$ alkanediyl, which may be unsubstituted or substituted by OH;
$X^{21}$, $X^{22}$ are independently selected from
 (a) $X^1$, which may be further substituted by —$X^5$—$COOR^{12}$, —$X^5$—$SO_2$—O—$R^{12}$, a $C_2$ to $C_6$ polyoxyalkylene group of formula —(O—$CH_2$—$CHR^{11}$)$_z$—OH, or a combination thereof, and
 (b) —$X^1$—NH—CO—$X^6$—CO—NH—$X^1$—;
$X^{31}$, $X^{32}$ are independently selected from a chemical bond and $X^1$;
$X^{41}$, $X^{42}$ are independently selected from $X^1$;
$X^5$ is a linear or branched $C_1$ to $C_{10}$ alkyl;
$X^6$ is selected from $X^1$ and a divalent 5 or 6 membered aromatic group;
$R^1$, $R^2$ are independently selected from a monovalent 5 or 6 membered aromatic N-heterocyclic group comprising one or two N atoms which are separated by at least one C atom, and its derivatives received by N-alkylation with a $C_1$-$C_6$-alkyl group, which may be substituted by —$COOR^{12}$ or —$SO_2$—O—$R^{12}$, and which aromatic N-heterocyclic group may optionally further comprise, under the proviso that $X^{21}$ is substituted by at least one OH, one S atom;
$R^3$, $R^4$ are independently selected from a monovalent 5 or 6 membered aliphatic N-heterocyclic group comprising one N atom and one O atom;
$D^1$ is independently selected from S, O and $NR^{10}$;
$D^2$ is (a) a divalent 5 or 6 membered aliphatic heterocyclic ring system comprising 1 or 2 S atoms, or (b) a 5 or 6 membered aromatic heterocyclic ring system comprising at least two N atoms and optionally one or two S atoms;
$D^3$ is independently selected from S and $NR^{10}$;
n is an integer of from 0 to 5;
z is an integer from 1 to 50;
$R^{10}$ is selected from H and a linear or branched $C_1$-$C_{12}$ alkyl;
$R^{11}$ is selected from H and a linear or branched $C_1$ to $C_6$ alkyl; and
$R^{12}$ is selected from $R^{10}$ and a cation.

With the aid of the complexing agents the plating baths are stable over a long time without showing coloring or deposits and are capable of electrodepositing tin-silver alloys on semiconductor substrates, particularly tin-silver alloy solder bumps.

The invention further relates to the use of a tin-silver alloy plating bath comprising a composition as defined herein for depositing tin-silver alloys on a substrate comprising features having an aperture size of 500 nm to 500 μm.

The invention further relates to a process for depositing a tin-silver alloy layer on a substrate by
 a) contacting a composition as defined herein with the substrate, and
 b) applying a current to the substrate for a time sufficient to deposit a tin or tin alloy layer onto the substrate,
wherein the substrate comprises features having an aperture size of 500 nm to 500 μm and the deposition is performed to fill these features.

The Invention further relates to a compound of formula C1, C2 or C3

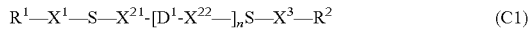  (C1)

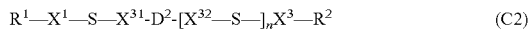  (C2)

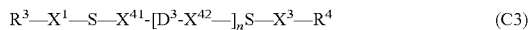  (C3)

wherein
$X^1$, $X^3$ are independently selected from a linear or branched $C_1$-$C_{12}$ alkanediyl, which may be unsubstituted or substituted by OH;
$X^{21}$, $X^{22}$ are independently selected from
  (a) $X^1$, which may be further substituted by $-X^5-COOR^{12}$, $-X^5-SO_2-O-R^{12}$, a $C_2$ to $C_6$ polyoxyalkylene group of formula $-(O-CH_2-CHR^{11})_z-OH$, or a combination thereof, and
  (b) $-X^1-NH-CO-X^6-CO-NH-X^1-$;
$X^{31}$, $X^{32}$ are independently selected from a chemical bond and $X^1$;
$X^{41}$, $X^{42}$ are independently selected from $X^1$;
$X^5$ is a linear or branched $C_1$ to $C_{10}$ alkyl;
$X^6$ is selected from $X^1$ and a divalent 5 or 6 membered aromatic group;
$R^1$, $R^2$ are independently selected from a monovalent 5 or 6 membered aromatic N-heterocyclic group comprising one N atom or two N atoms which are separated by at least one C atom, and its derivatives received by N-alkylation with a $C_1$-$C_6$-alkyl group, which may be substituted by $-COOR^{12}$ or $-SO_2-O-R^{12}$, and which aromatic N-heterocyclic group may optionally further comprise, under the proviso that $X^{21}$ is substituted by at least one OH, one S atom;
$R^3$, $R^4$ are independently selected from a monovalent 5 or 6 membered aliphatic N-heterocyclic group comprising one N atom and one O atom;
$D^1$ is independently selected from S, O and $NR^{10}$;
$D^2$ is (a) a divalent 5 or 6 membered aliphatic heterocyclic ring system comprising 1 or 2 S atoms, or (b) a 5 or 6 membered aromatic heterocyclic ring system comprising at least two N atoms and optionally one or two S atoms;
$D^3$ is independently selected from S and $NR^{10}$;
n is an integer of from 0 to 5;
z is an integer from 1 to 50;
$R^{10}$ is selected from H and a linear or branched $C_1$-$C_{12}$ alkyl; and
$R^{11}$ is selected from H and a linear or branched $C_1$ to $C_6$ alkyl; and
$R^{12}$ is selected from $R^{10}$ and a cation.
excluding 1,8-Bis(2-pyridyl)-3,6-dithiaoctane; 1,9-Bis-(2-pyridyl)-2,5,8-trithianonane; 1,11-Bis(2-pyridyl)-3,6,9-trithiaundecane; 1,6-Bis-(2-pyridyl)-2,5-dithiahexane; 1,13-Bis(2-pyridyl)-2,5,9,12-tetrathiatridecane; 1,9-Bis(2-pyridyl)-5-oxa-2,8-dithianonane; 1,8-Bis(4-pyridyl)-3,6-dithiaoctane; 1-[2-[2-(2-imidazol-1-ylethylsulfanyl)ethylsulfanyl]ethyl]imidazole; 1-[2-[2-[2-(2-imidazol-1-ylethylsulfanyl)ethylsulfanyl]ethylsulfanyl]ethyl]imidazole; 1,9-Bis(2-pyridyl)-3,7-dithianonane; 1,10-Bis(2-pyridyl)-3,8-dithiadecane.

DETAILED DESCRIPTION OF THE INVENTION

Complexing Agents According to the Invention

It was found that compositions for tin-silver alloy electroplating according to the invention comprising at least one complexing agent as described below are stable over a long time without showing coloring or deposits and are capable of electrodepositing tin-silver alloys on semiconductor substrates, particularly tin-silver alloy solder bumps. Long time stability here means a stable bath over a period of at least 6 months.

Besides tin ions and silver ions the aqueous compositions, preferably solutions, according to the present invention comprises at least one compound of formula C1, C2 and C3, as further described below.

First Embodiment

The aqueous composition may comprise a complexing agent compound of formula C1:

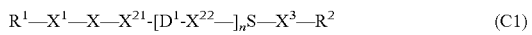  (C1)

wherein
$X^1$, $X^3$ are independently selected from a linear or branched $C_1$-$C_{12}$ alkanediyl, which may be unsubstituted or substituted by OH;
$X^{21}$, $X^{22}$ are independently selected from
  (a) $X^1$, which may be further substituted by $-X^5-COOR^{12}$, $-X^5-SO_2-O-R^{12}$, a $C_2$ to $C_6$ polyoxyalkylene group of formula $-(O-CH_2-CHR^{11})_z-OH$, or a combination thereof, and
  (b) $-X^1-NH-CO-X^6-CO-NH-X^1-$;
$X^5$ is a linear or branched $C_1$ to $C_{10}$ alkyl;
$X^6$ is selected from $X^1$ and a divalent 5 or 6 membered aromatic group;
$R^1$, $R^2$ are independently selected from a monovalent 5 or 6 membered aromatic N-heterocyclic group comprising one or two N atoms which are separated by at least one C atom, and its derivatives received by N-alkylation with a $C_1$-$C_6$-alkyl group, which may be substituted by $-COOR^{12}$ or $-SO_2-O-R^{12}$, and which aromatic N-heterocyclic group may optionally, under the proviso that $X^{21}$ is substituted by at least one OH, further comprise one S atom;
$D^1$ is independently selected from S, O and $NR^{10}$;
n is an integer of from 0 to 5;
z is an integer from 1 to 50;
$R^{10}$ is selected from H and a linear or branched $C_1$-$C_{12}$ alkyl; and
$R^{11}$ is selected from H and a linear or branched $C_1$ to $C_6$ alkyl; and
$R^{12}$ is selected from $R^{10}$ and a cation.
Essentially, such complexing agents comprise at least two sulfur atoms which are separated by at least a spacer group $X^{21}$ and which are terminated by 5 or 6 membered aromatic N-heterocyclic group comprising one or two N atoms, again separated by spacer groups $X^1$ and $X^3$.

Preferred spacer groups $X^1$ and $X^3$ may be linear or branched $C_1$-$C_8$ alkanediyl, more preferred $C_1$-$C_6$ alkanediyl, most preferably selected from methanediyl, ethanediyl, propanediyl, and butanediyl. Such alkanediyl may either be unsubstituted or substituted by hydroxy (OH) functional groups.

In a first alternative, preferred spacer groups $X^{21}$ and $X^{22}$ may be linear or branched $C_1$-$C_8$ alkanediyl, more preferred $C_1$-$C_6$ alkanediyl, most preferably $C_1$-$C_4$ alkanediyl. Such alkanediyl may either be unsubstituted or substituted by hydroxy (OH) functional groups. In contrast to spacer groups $X^1$ and $X^3$, spacer groups $X^{21}$ and, if applicable, $X^{22}$ may be further substituted by $-X^5-COOR^{12}$, or $-X^5-SO_2-O-R^{12}$, wherein $X^5$ is a linear or branched $C_1$ to $C_{10}$ alkyl, preferably a $C_1$ to $C_8$ alkyl, more preferably a $C_1$ to $C_6$ alkyl, most preferably a $C_2$ to $C_6$ alkyl.

Linear alkyl and alkyl with short $C_1$ or $C_2$ branches are preferred. spacer groups $X^{21}$ and, if applicable, $X^{22}$ may also be further substituted by one or more C2 to C6 polyoxyalkylene group of formula —(O—$CH_2$—$CHR^{11}$)$_z$—OH, wherein $R^{11}$ is selected from H and a linear or branched $C_1$ to $C_6$ alkyl, preferably H, ethyl, or propyl, most preferably H or methyl. z is an integer from 1 to 50, preferably from 1 to 30, even more preferably from 1 to 20, most preferably from 1 to 10. For more details, it is referred to the description of the polyoxyalkylene group in $R^{S11}$ of formula S1 below. Generally, if $R^{12}$ is H, groups —$COOR^{12}$, and —$X^5$—$SO_2$—O—$R^{12}$ may be deprotonated and $R^{12}$ would be cation. Useful cations are any cations that do not interfere with the complexing or electroplating, preferably metal cations or $NR^{10}_4{}^+$, most preferably $Na^+$, $K^+$, or tetramethyl ammonium.

In a second alternative, preferred spacer groups $X^{21}$ and $X^{22}$ may be —$X^1$—NH—CO—$X^6$—CO—NH—$X^1$—, wherein $X^6$ is selected from $X^1$ and a divalent 5 or 6 membered aromatic group. Preferred aliphatic groups $X^{21}$ and $X^{22}$ are methanediyl, ethanediyl, propanediyl or butanediyl. Preferred aromatic groups $X^{21}$ and $X^{22}$ are phenyl, imidazole, thiazole, and pyridine, most preferably phenyl.

In formula C1 n may be 0 or an integer from 1 to 5. If n is 0, the complexing agent comprises only two sulfur atoms. If n is greater than 0, one or more further heteroatoms $D^1$ are present. Preferably n is 0 or an integer from 1 to 4, more preferably 0 or an integer from 1 to 3, even mose preferably 0, 1 or 2, most preferably 0 or 1.

The heteroatoms/-groups $D^1$ may be S, O and $NR^{10}$, preferably S or O. Herein, $R^{10}$ is selected from H and a linear or branched $C_1$ to $C_{12}$ alkyl, preferably from H and a linear or branched $C_1$ to $C_6$ alkyl, most preferably from H, methyl, ethyl, propyl and butyl.

The termination groups $R^1$ and $R^2$ may be selected from a monovalent 5 or 6 membered aromatic N-heterocyclic group comprising one or two N atoms. The N atoms are separated by at least one C atom. Examples of 5 membered N-heterocyclic group are, without limitation, N-imidazole, N-pyrazol. Examples of 6 membered N-heterocyclic group are, without limitation, 2-pyridine, 3-pyridine, 4-pyridine, and 2-pyrazine.

Furthermore, the cationic derivatives received by N-alkylation with a $C_1$-$C_6$-alkyl group, preferably alkylation with methyl, ethyl, propyl or butyl may be used in the plating bath according to the invention. Examples of such cationic N-heterocyclic group are, without limitation, N-alkyl-pyridinium cations. Any suitable anion, such as but not limited to sulfate and methane sulfonate may be used in combination with the cations.

In an alternative within the first embodiment the aromatic N-heterocyclic group further comprises, one S atom. However, in this embodiment it is required that the spacer group $X^1$ (including all spacer groups $X^{21}$ and $X^{22}$ partly incorporating $X^1$) is substituted by at least one OH functional group. Examples of 5 membered N-heterocyclic groups comprising sulfur are 2-thiazole, thiadiazol, and isothiazol.

Without limitation, particularly preferred compounds according to the first embodiment are:

| $R^1$, $R^2$ | $D^1$ | $X^1$ | $X^3$ | $X^{21}$, $X^{22}$ | n |
| --- | --- | --- | --- | --- | --- |
| N-Imidazole |   | Et | Et | E | 0 |
| N-Imidazole | S | Me | Me | Et | 1 |
| N-Imidazole | S | Et | Et | Et | 1 |
| N-Imidazole |   | Me | Me | Et | 0 |
| N-Imidazole | S | Me | Me | Et | 2 |
| N-Imidazole | S | Et | Et | Et | 2 |
| N-Imidazole |   | Et | Et | cis-Bu(OH)$_2$ | 0 |
| N-Imidazole |   | Et | Et | trans-Bu(OH)$_2$ | 0 |
| N-Imidazole |   | Me | Me | cis-Bu(OH)$_2$ | 0 |
| N-Imidazole |   | Me | Me | trans-Bu(OH)$_2$ | 0 |
| N-Imidazole | O | Me | Me | Et | 1 |
| N-Imidazole | O | Et | Et | Et | 1 |
| N-Imidazole | O | Et | Et | Et | 2 |
| N-Imidazole | O | Et | Et | Et, Pr(Et)(MeOH) | 2 |
| N-Imidazole |   | Et | Et | Pr—OH | 0 |
| N-Imidazole |   | Et | Et | iPr(OH) | 0 |
| N-Imidazole |   | Et | Et | Pr(BuCOOH) | 0 |
| N-Imidazole |   | Et | Et | Et | 0 |
| N-Imidazole | S | Pr | Pr | Et | 1 |
| N-Imidazole |   | Pr | Pr | Bu(OH)$_2$ | 0 |
| N-Imidazole |   | Et | Et | Bu(OH)$_2$ | 0 |
| N-Imidazole |   | Et | Et | Pr | 0 |
| N-Imidazole |   | Et | Et | Pe | 0 |
| N-Imidazole | O | Pr | Pr | Pr, Pr—OH, Pr | 2 |
| N-Imidazole |   | Et | Et | Et—SO$_3$H or Et—SO$_3$Na | 0 |
| N-Imidazole |   | Et | Et | Bu[(EO)$_5$]$_2$ | 0 |
| N-Imidazole |   | Et | Et | Bu[(EO)$_{30}$]$_2$ | 0 |
| N-Imidazole |   | Et | Et | Bu[(EO)$_5$(PO)$_5$]$_2$ | 0 |
| N-Imidazole |   | Et | Et | —Et—NH—CO—Ph—CO—NH—Et— | 0 |
| 2-Pyrazine |   | Et | Et | Et | 0 |
| 2-Pyrazine | S | Me | Me | Et | 1 |
| 2-Pyrazine | S | Et | Et | Et | 1 |
| 2-Pyrazine |   | Me | Me | Et | 0 |
| 2-Pyrazine | S | Me | Me | Et | 2 |
| 2-Pyrazine | S | Et | Et | Et | 2 |
| 2-Pyrazine |   | Et | Et | cis-Bu(OH)$_2$ | 0 |
| 2-Pyrazine |   | Et | Et | trans-Bu(OH)$_2$ | 0 |
| 2-Pyrazine |   | Me | Me | cis-Bu(OH)$_2$ | 0 |
| 2-Pyrazine |   | Me | Me | trans-Bu(OH)$_2$ | 0 |

-continued

| R¹, R² | D¹ | X¹ | X³ | X²¹, X²² | n |
|---|---|---|---|---|---|
| 2-Pyrazine | O | Me | Me | Et | 1 |
| 2-Pyrazine | O | Et | Et | Et | 1 |
| 2-Pyrazine | O | Et | Et | Et | 2 |
| 2-Pyrazine | O | Et | Et | Et, Pr(Et)(MeOH) | 2 |
| 2-Pyrazine | | Et | Et | Pr—OH | 0 |
| 2-Pyrazine | | Et | Et | Bu(OH)$_2$ | 0 |
| 2-Pyrazine | | Et | Et | iPr(OH) | 0 |
| 2-Pyrazine | | Et | Et | Pr(BuCOOH) | 0 |
| 2-Pyrazine | | Me | Me | Pr | 0 |
| 2-Pyrazine | | Me | Me | Pe | 0 |
| 2-Pyrazine | | Et | Et | Pr | 0 |
| 2-Pyrazine | | Et | Et | Pe | 0 |
| 2-Pyrazine | O | Pr | Pr | Pr, Pr—OH, Pr | 2 |
| 2-Pyrazine | | Et | Et | Et—SO$_3$H or Et—SO$_3$Na | 0 |
| 2-Pyrazine | | Et | Et | Bu[(EO)$_5$]$_2$ | 0 |
| 2-Pyrazine | | Et | Et | Bu[(EO)$_{30}$]$_2$ | 0 |
| 2-Pyrazine | | Et | Et | Bu[(EO)$_5$(PO)$_5$]$_2$ | 0 |
| 2-Pyrazine | | Et | Et | —Et—NH—CO—Ph—CO—NH—Et— | 0 |
| 2-Thiazole | | Et | Et | Et | 0 |
| 2-Thiazole | S | Me | Me | Et | 1 |
| 2-Thiazole | S | Et | Et | Et | 1 |
| 2-Thiazole | | Me | Me | Et | 0 |
| 2-Thiazole | S | Me | Me | Et, Pr | 2 |
| 2-Thiazole | S | Et | Et | Et, Pr | 2 |
| 2-Thiazole | | Et | Et | cis-Bu(OH)$_2$ | 0 |
| 2-Thiazole | | Et | Et | trans-Bu(OH)$_2$ | 0 |
| 2-Thiazole | | Me | Me | cis-Bu(OH)$_2$ | 0 |
| 2-Thiazole | | Me | Me | trans-Bu(OH)$_2$ | 0 |
| 2-Thiazole | O | Me | Me | Et | 1 |
| 2-Thiazole | O | Et | Et | Et | 1 |
| 2-Thiazole | O | Et | Et | Et | 2 |
| 2-Thiazole | O | Et | Et | Et, Pr(Et)(MeOH) | 2 |
| 2-Thiazole | | Et | Et | Pr—OH | 0 |
| 2-Thiazole | | Et | Et | iPr(OH) | 1 |
| 2-Thiazole | | Et | Et | Pr(BuCOOH) | 1 |
| 2-Thiazole | | i-Pr | i-Pr | trans-Bu(OH)$_2$ | 0 |
| 2-Thiazole | | i-Pr | i-Pr | cis-Bu(OH)$_2$ | 0 |
| 2-Thiazole | | Et | Et | Pr | 0 |
| 2-Thiazole | | Et | Et | Pe | 0 |
| 2-Pyridine | | Et | Et | Et | 0 |
| 2-Pyridine | S | Me | Me | Et | 1 |
| 2-Pyridine | S | Et | Et | Et | 1 |
| 2-Pyridine | | Me | Me | Et | 0 |
| 2-Pyridine | S | Me | Me | Et, Pr | 2 |
| 2-Pyridine | S | Et | Et | Et, Pr | 2 |
| 2-Pyridine | | Et | Et | cis-Bu(OH)$_2$ | 0 |
| 2-Pyridine | | Et | Et | trans-Bu(OH)$_2$ | 0 |
| 2-Pyridine | | Me | Me | cis-Bu(OH)$_2$ | 0 |
| 2-Pyridine | | Me | Me | trans-Bu(OH)$_2$ | 0 |
| 2-Pyridine | O | Me | Me | Et | 1 |
| 2-Pyridine | O | Et | Et | Et | 1 |
| 2-Pyridine | O | Et | Et | Et | 2 |
| 2-Pyridine | O | Et | Et | Et, Pr(Et)(MeOH) | 2 |
| 2-Pyridine | | Et | Et | Pr—OH | 0 |
| 2-Pyridine | | Et | Et | Bu | 0 |
| 2-Pyridine | | Et | Et | Pe | 0 |
| 2-Pyridine | | Et | Et | iPr(OH) | 0 |
| 2-Pyridine | | Et | Et | Pr(BuCOOH) | 0 |
| 2-Pyridine | | Et | Et | Pr | 0 |
| 2-Pyridine | O | Pr | Pr | Pr, Pr—OH, Pr | 2 |
| 2-Pyridine | | Et | Et | Et—SO$_3$H or Et—SO$_3$Na | 0 |
| 2-Pyridine | | Et | Et | Bu[(EO)$_5$]$_2$ | 0 |
| 2-Pyridine | | Et | Et | Bu[(EO)$_{30}$]$_2$ | 0 |
| 2-Pyridine | | Et | Et | Bu[(EO)$_5$(PO)$_5$]$_2$ | 0 |
| 2-Pyridine | | Et | Et | —Et—NH—CO—Ph—CO—NH—Et— | 0 |
| 3-Pyridine | | Et | Et | trans-Bu(OH)$_2$ | 0 |
| 3-Pyridine | | Et | Et | cis-Bu(OH)$_2$ | 0 |
| 3-Pyridine | | Me | Me | cis-Bu(OH)$_2$ | 0 |
| 3-Pyridine | | Me | Me | trans-Bu(OH)$_2$ | 0 |
| 3-Pyridine | | Et | Et | Et | 0 |
| 3-Pyridine | O | Et | Et | Et | 1 |
| 3-Pyridine | O | Et | Et | Et | 2 |
| 3-Pyridine | S | Et | Et | Et | 1 |
| 3-Pyridine | S | Et | Et | Et, Pr | 2 |
| 3-Pyridine | | Et | Et | Bu | 0 |
| 3-Pyridine | | Et | Et | Pe | 0 |
| 3-Pyridine | S | Me | Me | Et | 1 |

-continued

| $R^1, R^2$ | $D^1$ | $X^1$ | $X^3$ | $X^{21}, X^{22}$ | n |
|---|---|---|---|---|---|
| 3-Pyridine | S | Me | Et | Et | 2 |
| 3-Pyridine | O | Me | Me | Et | 1 |
| 3-Pyridine | O | Me | Me | Et | 2 |
| 3-Pyridine | | Et | Et | Pr | 0 |
| 4-Pyridine | | Et | Et | trans-Bu(OH)$_2$ | 0 |
| 4-Pyridine | | Et | Et | cis-Bu(OH)$_2$ | 0 |
| 4-Pyridine | | Me | Me | cis-Bu(OH)$_2$ | 0 |
| 4-Pyridine | | Me | Me | trans-Bu(OH)$_2$ | 0 |
| 4-Pyridine | | Et | Et | Et | 0 |
| 4-Pyridine | O | Et | Et | Et | 1 |
| 4-Pyridine | O | Et | Et | Et | 2 |
| 4-Pyridine | S | Et | Et | Et | 1 |
| 4-Pyridine | S | Et | Et | Et, Pr | 2 |
| 4-Pyridine | | Et | Et | Bu | 0 |
| 4-Pyridine | | Et | Et | Pe | 0 |
| 4-Pyridine | S | Me | Me | Et | 1 |
| 4-Pyridine | S | Me | Et | Et | 2 |
| 4-Pyridine | O | Me | Me | Et | 1 |
| 4- Pyridine | O | Me | Me | Et | 2 |
| 4- Pyridine | | Et | Et | Pr | 0 |
| 2-Me—N-Pyridinium$^{+-}$ | | Et | Et | Et | 0 |
| 2-O$_3$S—Me—N-Pyridinium | | Me | Me | Et | 0 |
| 2-O$_3$S—Et—N-Pyridinium | | Et | Et | Et | 0 |
| 2-O$_3$S—Pr—N-Pyridinium | | Et | Et | Et | 0 |
| 2-O$_3$S—Pr—N-Pyridinium | | Et | Et | trans-Bu(OH)$_2$ | 0 |
| 2-O$_3$S—Pr—N-Pyridinium | | Et | Et | cis-Bu(OH)$_2$ | 0 |

Abbreviations:
Me = Methyl/Methanediyl;
Et = Ethyl/Ethanediyl;
Pr = Propyl/Propanediyl;
Bu = Butyl/Butanediyl;
Pe = Pentyl/Pentanediyl;
Bu(OH)$_2$ = 2,3-dihydroxy butanediyl,
i-Pr = Isopropanediyl;
Pr(Et)(MeOH) = 2-ethyl,2-hydroxyethyl propanediyl,
Pr(BuCOOH) = 2-carboxybutyl propanediyl,
Ph = phenyl,
EO = oxyethylene,
PO = oxypropylene,
2-O$_3$S—Me—N-Pyridinium = 2-pyridine quaternized with methyl that comprises a sulfonic acid substituent.

Second Embodiment

The aqueous composition may comprise a complexing agent compound of formula C2:

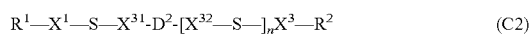
$$R^1-X^1-S-X^{31}-D^2-[X^{32}-S-]_nX^3-R^2 \quad (C2)$$

wherein
$X^1, X^3$ are independently selected from a linear or branched $C_1$-$C_{12}$ alkanediyl, which may be unsubstituted or substituted by OH;
$X^{31}, X^{32}$ are independently selected from a chemical bond and $X^1$;
$R^1, R^2$ are independently selected from a monovalent 5 or 6 membered aromatic N-heterocyclic group comprising one or two N atoms which are separated by at least one C atom, and its derivatives received by N-alkylation with a $C_1$-$C_6$-alkyl group, which aromatic N-heterocyclic group may optionally further comprise one S atom;
$D^2$ is (a) a divalent 6 membered aliphatic heterocyclic ring system comprising 1 or 2 S atoms, or (b) a 5 or 6 membered aromatic heterocyclic ring system comprising at least two N atoms and optionally one or two S atoms;
n is an integer of from 0 to 5;
$R^{10}$ is selected from H and a linear or branched $C_1$-$C_{12}$ alkyl.

Again, such complexing agents comprise at least two sulfur atoms which are separated by a spacer group $X^{31}$ and which are terminated by 5 or 6 membered aromatic N-heterocyclic group comprising one or two N atoms, again separated by spacer groups $X^1$ and $X^3$. In contrast to the first embodiment, the second (or third) sulfur atom is incorporated in either a divalent 6 membered aliphatic heterocyclic ring system comprising 1 or 2 S atoms, or a 5 or 6 membered aromatic heterocyclic ring system comprising at least two N atoms and optionally one or two S atoms.

Preferred spacer groups $X^1$ and $X^3$ may be linear or branched $C_1$-$C_8$ alkanediyl, more preferred $C_1$-$C_6$ alkanediyl, most preferably selected from methanediyl, ethanediyl, propanediyl, and butanediyl. Such alkanediyl may either be unsubstituted or substituted by hydroxy (OH) functional groups.

Preferred spacer groups $X^{31}$ and $X^{32}$ may be linear or branched $C_1$-$C_8$ alkanediyl, more preferred $C_1$-$C_6$ alkanediyl, most preferably $C_1$-$C_4$ alkanediyl. Alternatively, and also preferred, $X^{31}$ and $X^{32}$ may be a chemical bond. Such alkanediyl may either be unsubstituted or substituted by hydroxy (OH) functional groups. Linear alkyl is preferred.

n may be 0 or an integer from 1 to 5. If n is 0, the complexing agent comprises only one sulfur atom in the main chain and optionally one or more sulfur atoms in the ring system $D^2$. If n is greater than 0, one or more further sulfur atoms are present in the main chain. Preferably n is 0 or an integer from 1 to 4, more preferably 0 or an integer from 1 to 3, most preferably 0, 1 or 2.

In one alternative, the ring system $D^2$ may be a divalent 5 or 6 membered aliphatic heterocyclic ring system comprising 1 or 2 S atoms. Such aliphatic heterocyclic systems may further comprise O atoms or N—$R^{10}$ groups. Preferably, the 5-membered aliphatic heterocyclic ring systems have 2 S atoms or 1 S and one N atom. More preferably $D^2$ is selected from Dithiolane and Thiazolidine. Preferably, the 6-membered aliphatic heterocyclic ring system have 2 S atoms or 1 S and one N atom. Most preferred ring systems $D^2$ are dithiane, particularly 2,5 dithiane, and thiomorpholine.

In another alternative, the ring system $D^2$ may also be a 5 or 6 membered aromatic heterocyclic ring system comprising at least two N atoms and optionally one or two S atoms. Such aromatic heterocyclic systems may further comprise an O atom or a carbonyl group. Most preferred ring systems $D^2$ are Amino-1,3,5-Triazin and 1,3,4-thiadiazole-2-thione.

Like the first embodiment, the termination groups $R^1$ and $R^2$ may be selected from a monovalent 5 or 6 membered aromatic N-heterocyclic group comprising one or two N atoms. Examples of 5 membered N-heterocyclic group are, without limitation, N-imidazole, N-pyrazol, and 2-thiazole. Preferred are N-imidazole and N-pyrazol. Examples of 6 membered N-heterocyclic group are, without limitation, 2-pyridine, 3-pyridine, 4-pyridine, and 2-pyrazine. Preferred are 2-pyridine, 4-pyridine, and 2-pyrazine.

In an alternative within the third embodiment the aromatic N-heterocyclic group further comprises, one S atom. Examples of 5 membered N-heterocyclic group comprising sulfur are 2-Thiazole, Thiadiazol, and Isothiazol.

Like the first embodiment, the cationic derivatives received by N-alkylation with a $C_1$-$C_6$-alkyl group, preferably alkylation with methyl, ethyl, propyl or butyl may be used in the plating bath according to the invention. Examples of such cationic N-heterocyclic group are, without limitation, N-methyl-pyridinium cations. Any suitable anion, such as but not limited to sulfate and methane sulfonate may be used in combination.

Particularly preferred compounds according to the second embodiment are:

| $R^1$, $R^2$ | $D^2$ | $X^1$ | $X^3$ | $X^{31}$, $X^{32}$ | n |
|---|---|---|---|---|---|
| N-Imidazole | 1,3,4-thiadiazole-2-thione | Et | Et | bond | 0 |
| N-Imidazole | 2,5 dithiane | Et | Et | Me | 1 |
| N-Imidazole | 2,5 dithiane | Me | Me | Me | 1 |
| N-Imidazole | 2,5 dithiane | Pr | Pr | Me | 1 |
| N-Imidazole | 2,5 dithiane | Et | Et | Et | 1 |
| N-Imidazole | Amino-1,3,5-Triazine | Et | Et | bond | 1 |
| N-Imidazole | Amino-1,3,5-Triazine | Me | Me | bond | 1 |
| N-Imidazole | 1,3,5-Triazine | Et | Et | bond | 1 |
| 2-Pyrazine | 1,3,4-thiadiazole-2-thione | Et | Et | bond | 0 |
| 2-Pyrazine | 2,5 dithiane | Et | Et | Me | 1 |
| 2-Pyrazine | Amino-1,3,5-Triazine | Et | Et | bond | 1 |
| 2-Pyrazine | Amino-1,3,5-Triazine | Me | Me | bond | 1 |
| 2-Pyrazine | 1,3,5-Triazine | Et | Et | bond | 1 |
| 2-Thiazole | 1,3,4-thiadiazole-2-thione | Et | Et | bond | 0 |
| 2-Thiazole | 2,5 dithiane | Et | Et | Me | 1 |
| 2-Thiazole | Amino-1,3,5-Triazine | Et | Et | bond | 1 |
| 2-Thiazole | Amino-1,3,5-Triazine | Me | Me | bond | 1 |
| 2-Thiazole | 1,3,5-Triazine | Et | Et | bond | 1 |
| 2-Pyridine | 1,3,4-thiadiazole-2-thione | Et | Et | bond | 0 |
| 2-Pyridine | 2,5 dithiane | Et | Et | Me | 1 |
| 2-Pyridine | Amino-1,3,5-Triazine | Et | Et | bond | 1 |
| 2-Pyridine | Amino-1,3,5-Triazine | Me | Me | bond | 1 |
| 2-Pyridine | 1,3,5-Triazine | Et | Et | bond | 1 |
| 3-Pyridine | 1,3,4-thiadiazole-2-thione | Et | Et | bond | 0 |
| 3-Pyridine | 2,5 dithiane | Et | Et | Me | 1 |
| 3-Pyridine | Amino-1,3,5-Triazine | Et | Et | bond | 1 |
| 3-Pyridine | Amino-1,3,5-Triazine | Me | Me | bond | 1 |
| 3-Pyridine | 1,3,5-Triazine | Et | Et | bond | 1 |
| 4-Pyridine | 1,3,4-thiadiazole-2-thione | Et | Et | bond | 0 |
| 4-Pyridine | 2,5 dithiane | Et | Et | Me | 1 |
| 4-Pyridine | Amino-1,3,5-Triazine | Et | Et | bond | 1 |
| 4-Pyridine | Amino-1,3,5-Triazine | Me | Me | bond | 1 |
| 4-Pyridine | 1,3,5-Triazin | Et | Et | bond | 1 |

Abbreviations:
Me = Methyl/Methanediyl,
Et = Ethyl/Ethanediyl;
Bu(OH)$_2$ = 2,3-dihydroxy butanediyl,
Pr = Propyl/Propanediyl Third Embodiment The aqueous composition may comprise a complexing agent compound of formula C3:

$$R^3—X^1—S—X^{41}-[D^3-X^{42}—]_n S—X^3—R^4 \quad (C3)$$

wherein
$X^1$, $X^3$ are independently selected from a linear or branched $C_1$-$C_{12}$ alkanediyl, which may be unsubstituted or substituted by OH;
$X^{41}$, $X^{42}$ are independently selected from $X^1$;
$R^3$, $R^4$ are independently selected from a monovalent 5 or 6 membered aliphatic N-heterocyclic group comprising one N atom and one O atom;
$D^3$ is selected from S and $NR^{10}$;
n is an integer of from 0 to 5;
$R^{10}$ is selected from H and a linear or branched $C_1$-$C_{12}$ alkyl.

Like the first embodiment, such complexing agents comprise at least two sulfur atoms which are separated by at least a spacer group $X^{41}$ and optionally $X^{42}$, and which are terminated by 5 or 6 membered aliphatic N-heterocyclic group comprising one N and one O atom, again separated by spacer groups $X^1$ and $X^3$.

Preferred spacer groups $X^1$ and $X^3$ may be linear or branched $C_1$-$C_8$ alkanediyl, more preferred $C_1$-$C_6$ alkanediyl, most preferably $C_1$-$C_4$ alkanediyl. Such alkanediyl may either be unsubstituted or substituted by hydroxy (OH) functional groups.

Preferred spacer groups $X^{41}$ and $X^{42}$ may be linear or branched $C_1$-$C_8$ alkanediyl, more preferably $C_1$-$C_6$ alkanediyl, most preferably $C_1$-$C_4$ alkanediyl. Such alkanediyl may either be unsubstituted or substituted by hydroxy (OH) functional groups. Linear alkyl is preferred.

n may be 0 or an integer from 1 to 5. If n is 0, the complexing agent comprises only two sulfur atoms. If n is greater than 0, one or more further heteroatoms $D^1$ are present. Preferably n is 0 or an integer from 1 to 4, more preferably 0 or an integer from 1 to 3, most preferably 0, 1 or 2.

The heteroatoms/-groups $D^3$ may be selected from S and $NR^{10}$, preferably S. Herein, $R^{10}$ is selected from H and a linear or branched $C_1$ to $C_{12}$ alkyl, preferably from H and a linear or branched $C_1$ to $C_6$ alkyl, most preferably from H, methyl, ethyl, propyl and butyl.

The termination groups $R^3$ and $R^4$ may be selected from a monovalent 5 or 6 membered aliphatic N-heterocyclic group comprising one N atom and one O atom incorporated in the ring system or attached to the ring system, such as but not limited to C=O groups. Examples of 5 membered heterocyclic group are, without limitation, N-pyrrolidone, N-oxazolidine, succinimide, and N-hydroxy succinimide. Preferred is N-pyrrolidone. An examples of a 6 membered heterocyclic group is, without limitation, N-morpholine.

Particularly preferred complexing agents are:

| $R^3$, $R^4$ | $D^3$ | $X^1$ | $X^3$ | $X^{41}$, $X^{42}$ | n |
|---|---|---|---|---|---|
| N-Morpholine |   | Et | Et | Bu(OH)$_2$ | 0 |
| N-Morpholine |   | Et | Et | Et | 0 |
| N-Morpholine |   | Me | Me | Me | 0 |
| N-Morpholine |   | Me | Me | Bu(OH)$_2$ | 0 |
| N-Morpholine | S | Et | Et | Bu(OH)$_2$ | 1 |
| N-Morpholine | S | Et | Et | Et | 1 |
| N-Morpholine | S | Me | Me | Me | 1 |
| N-Morpholine | S | Me | Me | Bu(OH)$_2$ | 1 |
| N-Pyrrolidone |   | Et | Et | Bu(OH)$_2$ | 0 |
| N-Pyrrolidone |   | Et | Et | Et | 0 |
| N-Pyrrolidone |   | Me | Me | Me | 0 |
| N-Pyrrolidone |   | Me | Me | Bu(OH)$_2$ | 0 |
| N-Pyrrolidone | S | Et | Et | Bu(OH)$_2$ | 1 |
| N-Pyrrolidone | S | Et | Et | Et | 1 |
| N-Pyrrolidone | S | Me | Me | Me | 1 |
| N-Pyrrolidone | S | Me | Me | Bu(OH)$_2$ | 1 |

Particular complexing agents are those selected from:
(a) if n=0, $X^{21}$ is substituted by at least one, preferably two OH; and
(b) if n is 1, $D^1$ is O or $NR^{10}$ and, if $X^1$ and $X^3$ are methanediyl, at least one of $R^1$ and $R^2$ is not 2-pyridiyl; and
(c) if n is greater than 1, $D^1$ is O or $NR^{10}$.

Most preferred complexing agents are selected from: 1,9-Bis-(3-pyridyl)-2,5,8-trithianonane; 1,15-Bis(2-pyridyl)-3,6,10,13-tetrathiapentadecane; (2R,3R)-1,4-bis[2-(2-pyridyl)ethylsulfanyl]butane-2,3-diol; (2S,3S)-1,4-bis[2-(2-pyridyl)-ethylsulfanyl]butane-2,3-diol; (2R,3S)-1,4-bis[2-(2-pyridyl)ethylsulfanyl]butane-2,3-diol; 1,6-Bis(2-methylpyridyl)-DL-dithiothreitol; 1,6-Bis(2-methylpyridyl)-meso-dithioerythritol; 1,11-Bis(2-pyridyl)-6-oxa-3,9-dithiaundecane; 1,14-Bis(2-pyridyl)-6,9-dioxa-3,12-dithiatetradecane; 1,11-Bis(4-pyridyl)-6-oxa-3,9-dithiaundecane; 1,14-Bis(4-pyridyl)-6,9-dioxa-3,12-dithiatetradecane; 1,11-Bis(4-pyridyl)-3,6,9-trithiaundecane; 1,15-Bis(4-pyridyl)-3,6,10,13-tetrathiapentadecane; (2R,3S)-1,4-bis[2-(4-pyridyl)ethylsulfanyl]butane-2,3-diol; 1-methyl-2-[2-[2-[2-(1-methylpyridin-1-ium-2-yl)-ethylsulfanyl]ethylsulfanyl]ethyl]pyridin-1-ium methylsulfate; 1,13-Bis(3-pyridyl)-2,5,9,12-tetrathiatridecane; 1,9-Bis-(4-pyridyl)-2,5,8-trithianonane; 1,13-Bis(4-pyridyl)-2,5,9,12-tetrathiatridecane, 1-[3-[2-[2-(3-imidazol-1-ylpropylsulfanyl)ethylsulfanyl]ethylsulfanyl]propyl]imidazole; 1,9-Bis(4-pyridyl)-5-oxa-2,8-dithianonane; (2S,3R)-1,4-bis(3-imidazol-1-ylpropylsulfanyl)butane-2,3-diol, (2R,3S)-1,4-bis(2-morpholinoethylsulfanyl)butane-2,3-diol; 4-[2-[2-[2-(4-pyridyl-methylsulfanyl)ethoxy]ethoxy]ethylsulfanylmethyl]pyridine; (2R,3S)-1,4-bis(2-imidazol-1-ylethyl-sulfanyl)butane-2,3-diol; 1-[2-[(2R,3S)-2,3-dihydroxy-4-[2-(2-oxopyrrolidin-1-yl)ethylsulfanyl]-butyl]sulfanylethyl]-pyrrolidin-2-one; 2,2-bis[3-[2-(2-pyridyl)ethylsulfanyl]propoxymethyl]butan-1-ol; 1-[2-[2-[2-[2-(2-oxopyrrolidin-1-yl)ethylsulfanyl]ethylsulfanyl]ethylsulfanyl]ethyl]pyrrolidin-2-one; (2R,3S)-1,4-bis(2-pyrazin-2-ylethylsulfanyl)butane-2,3-diol; (2S,3S)-1,4-bis[2-(4-pyridyl)-ethylsulfanyl]butane-2,3-diol; (2R,3R)-1,4-bis[2-(4-pyridyl)ethylsulfanyl]butane-2,3-diol; 3-[2-(2-pyridyl)ethyl]-5-[2-(2-pyridyl)ethylsulfanyl]-1,3,4-thiadiazole-2-thione; 2,3-bis[2-(2-pyridyl)ethyl-sulfanyl]propan-1-ol; 6,8-bis[2-(2-pyridyl)ethylsulfanyl]octanoic acid; 2-[2-[[5-[2-(2-pyridyl)-ethylsulfanylmethyl]-1,4-dithian-2-yl]methylsulfanyl]ethyl]pyridine; 4,6-bis[2-(2-pyridyl)ethyl-sulfanyl]-1,3,5-triazin-2-amine; (2R,3S)-1,4-bis(2-thiazol-2-ylpropylsulfanyl)butane-2,3-diol; 3-[2-[2-[(2S,3R)-2,3-dihydroxy-4-[2-[1-(3-sulfonatopropyl)pyridine-1-ium-2-yl]ethylsulfanyl] butyl]sulfanylethyl]pyridine-1-ium-1-yl]propane-1-sulfonate; 3-[2-[2-[2-[2-[1-(3-Sulfonatopropyl)pyridine-1-ium-2-yl]ethylsulfanyl]ethylsulfanyl]ethyl]pyridine-1-ium-1-yl]propane-1-sulfonate; 1,3-Bis[3-[2-(2-pyridyl)ethylsulfanyl]propoxy]propane-2-ol; N1,N3-bis[2-[2-(2-Pyridyl)ethylsulfanyl]ethyl]benzene-1,3-dicarboxamide; 2,3-Bis[2-(2-pyridyl)ethylsulfanyl]-propane-1-sulfonate; 2-[2-[5-[2-(2-Pyridyl)ethylsulfanyl]pentylsulfanyl]ethyl]pyridine; and their salts.

Other Complexing Agents

The tin or tin alloy electroplating bath may further contain additional complexing agents for complexing tin and/or any other metal present in the composition. A typical other complexing agent is 3,6-Dithia-1,8-octanediol.

Other typical complexing agents are polyoxy monocarboxylic acids, polycarboxylic acids, aminocarboxylic acids, lactone compounds, and salts thereof.

Other complexing agents are organic thiocompounds like thiourea, thiols or thioethers as disclosed in U.S. Pat. No. 7,628,903, JP 4296358 B2, EP 0854206 A and U.S. Pat. No. 8,980,077 B2.

It is preferred that the tin alloy bath comprises no other complexing agents except those according to the invention.

A large variety of additives may typically be used in the bath to provide desired surface finishes for the plated tin alloy bump. Usually more than one additive is used with each additive forming a desired function. Advantageously, the electroplating baths may contain one or more of suppressing agents (also often referred to as surfactants), grain refiners, complexing agents in case of alloy deposition, antioxidants, and mixtures thereof. Most preferably the electroplating bath comprises a leveler and optionally a grain refiner in addition to the suppressing agent according to the present invention. Other additives may also be suitably used in the present electroplating baths.

Suppressing Agents or Surfactants

One or more suppressing agents (also referred to as surfactants) may be present in the tin-silver alloy plating bath.

Any nonionic surfactant may be used in the present compositions. Typically, the nonionic surfactants have an average molecular weight from 200 to 100,000, preferably from 500 to 50,000, more preferably from 500 to 25,000, and yet more preferably from 750 to 15,000. Such nonionic surfactants are typically present in the electrolyte compositions in a concentration from 1 to 10,000 ppm, based on the weight of the composition, and preferably from 5 to 10,000 ppm. Preferred alkylene oxide compounds include polyalkylene glycols, such as but not limited to alkylene oxide addition products of an organic compound having at least one hydroxy group and 20 carbon atoms or less and tetrafunctional polyethers derived from the addition of different alkylene oxides to low molecular weight polyamine compounds.

Preferred polyalkylene glycols are polyethylene glycol and polypropylene glycol. Such polyalkylene glycols are generally commercially available from a variety of sources and may be used without further purification. Capped polyalkylene glycols where one or more of the terminal hydrogens are replaced with a hydrocarbyl group may also be suitably used. Examples of suitable polyalkylene glycols are those of the formula R—O—(CXYCX'Y'O)$_n$R' where R and R' are independently chosen from H, $C_2$-$C_{20}$ alkyl group and $C_6$-$C_{20}$ aryl group; each of X, Y, X' and Y' is independently selected from hydrogen, alkyl such as methyl, ethyl or propyl, aryl such as phenyl, or aralkyl such as benzyl; and n is an integer from 5 to 100,000. Typically, one or more of X, Y, X' and Y' is hydrogen.

Suitable EO/PO copolymers generally have a weight ratio of EO:PO of from 10:90 to 90:10, and preferably from 10:90 to 80:20. Such EO/PO copolymers preferably have an average molecular weight of from 750 to 15,000. Such EO/PO copolymers are available from a variety of sources, such as those available from BASF under the tradename "PLURONIC".

Suitable alkylene oxide condensation products of an organic compound having at least one hydroxy group and 20 carbon atoms or less include those having an aliphatic hydrocarbon from one to seven carbon atoms, an unsubstituted aromatic compound or an alkylated aromatic compound having six carbons or less in the alkyl moiety, such as those disclosed in U.S. Pat. No. 5,174,887. The aliphatic alcohols may be saturated or unsaturated. Suitable aromatic compounds are those having up to two aromatic rings. The aromatic alcohols have up to 20 carbon atoms prior to derivatization with ethylene oxide. Such aliphatic and aromatic alcohols may be further substituted, such as with sulfate or sulfonate groups.

Preferred surfactants are those of formula S1:

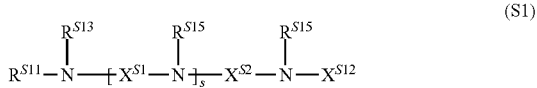

(S1)

The compounds of formula S1 may be prepared by reacting a polyamine starter with one or more $C_2$ to $C_6$ alkylene oxides to form the respective amine-based suppressing agents.

Generally, s may be an integer of from 1 to 6. Preferably s is an integer from 1 to 4, most preferably s is 1 or 2.

$X^{S1}$ and $X^{S2}$ are a divalent spacer group within the polyamine starter. They may independently be selected from a linear or branched $C_1$-$C_{12}$ alkanediyl. Such alkanediyl spacer are unsubstituted but may optionally be interrupted by O or S. $X^{S1}$ and $X^{S2}$ may be the same or different, preferably the same. In a first preferred embodiment $X^{S1}$ and $X^{S2}$ are $C_1$-$C_6$ alkanediyl, more preferably $C_1$-$C_4$ alkanediyl, most preferably methanediyl, ethanediyl or propanediyl. In a second preferred embodiment heteroatoms are present and $X^{S1}$ and $X^{S2}$ may be —(CHR$^{41}$)$_q$-[Q-(CHR$^{41}$)$_r$]$_v$—, with Q being selected from O or S wherein q+r·v is the number of C atoms in the spacer. Particularly preferred is a spacer with Q=O and q=r=1 or 2.

$R^{S11}$ is a monovalent group of formula —(O—CH$_2$—CHR$^{S41}$)$_m$—OR$^{S42}$, wherein m is an integer of from 2 to 250, preferably 3 to 120, most preferably 10 to 65. Since $R^{S11}$ may be prepared by polyalkoxylation of one or more alkylene oxides it is also referred to herein as "polyalkylene oxide" or "polyoxyalkylene". $R^{S41}$ is selected from H and a linear or branched $C_1$ to $C_5$ alkyl, preferably from H and a linear or branched $C_1$ to $C_3$ alkyl, more preferably from H, methyl, ethyl and n-propyl, most preferably from H or methyl. $R^{S42}$ is selected from H and a linear or branched $C_1$-$C_{20}$ alkyl, which may optionally be substituted by hydroxy, alkoxy or alkoxycarbonyl, preferably from H and a linear or branched $C_1$ to $C_{10}$ alkyl, more preferably from H and methyl, ethyl, propyl or butyl, most preferably H.

Generally, $R^{S12}$, $R^{S13}$, $R^{S14}$ are independently selected from H, $R^{S11}$ and $R^{S40}$, preferably from $R^{S11}$ and $R^{S40}$, most preferably from $R^{S11}$.

$R^{S40}$ is a linear or branched $C_1$-$C_{20}$ alkyl. Preferably $R^{S40}$ is $C_1$-$C_{10}$ alkyl, even more preferably $C_1$-$C_6$ alkyl, most preferably methyl, ethyl or propyl.

$R^{S42}$ is a linear or branched $C_1$-$C_{20}$ alkyl, which may optionally be substituted by hydroxy, alkoxy or alkoxycarbonyl. Preferably $R^{S42}$ is an unsubstituted linear or branched $C_1$-$C_{20}$ alkyl.

Generally, $R^{S15}$ is selected from H, $R^{S11}$, $R^{S40}$, and —$X^{S4}$—N(R$^{S21}$)$_2$ with $R^{S21}$ being selected from $R^{S11}$ and $R^{S40}$, preferably from $R^{S11}$.

In a preferred embodiment $R^{S15}$ is selected from $R^{S11}$ and —$X^{S4}$—N(R$^{S11}$)$_2$. In another preferred embodiment $R^{S15}$ is selected from $R^{S40}$ and —$X^{S4}$—N(R$^{S40}$)$_2$.

In one embodiment $X^{S4}$ is a linear or branched $C_1$ to $C_{12}$ alkanediyl. Preferably $X^{S4}$ is a $C_1$ to $C_6$ alkanediyl, more preferably methanediyl, ethanediyl, propanediyl or butanediyl, most preferably methanediyl or ethanediyl.

In another embodiment $X^{S4}$ is a divalent group which is selected from a $C_2$ to $C_6$ polyoxyalkylene group of formula —(O—CH$_2$—CHR$^{S41}$)$_o$— (hereinafter also referred to as polyalkylene oxide group). Herein o may be an integer from 1 to 250, preferably from 2 to 120, most preferably from 5 to 65. The $C_2$ to $C_6$ polyoxyalkylene group may be prepared from the one or more respective alkylene oxides. Preferably the at least one $C_2$ to $C_6$ polyoxyalkylene group is selected from polyoxyethylen (prepared from ethylene oxide), polyoxypropylene (prepared from propylene oxide), and polyoxybutylene (prepared from butylene oxide). More preferably the polyoxyalkylene group in $X^{S4}$ is a copolymer of ethylene oxide and at least one further $C_3$ to $C_6$ alkylene oxide. The further alkylene oxide is preferably selected from propylene oxide and 1,2-butylene oxide or any isomers thereof. In another preferred embodiment the $C_3$ to $C_4$ alkylene oxide is selected from propylene oxide (PO). In this case EO/PO copolymer side chains are generated from the starting molecule. Such copolymers of ethylene oxide and at least one further alkylene oxide may have random, block, alternating or any other arrangement.

As used herein, "random" means that the comonomers are polymerized from a mixture and therefore arranged in a statistically manner depending on their copoymerization parameters.

As used herein, "block" means that the comonomers are polymerized after each other to form blocks of the respective co-monomers in any predefined order. By way of example, for EO and propylene oxide (PO) comonomers such blocks may be, but are not limited to: -EO$_x$-PO$_y$-, -PO$_x$-EO$_y$-, -EO$_x$-PO$_y$-EO$_z$-, -PO$_x$-EO$_y$-PO$_z$-, etc. Preferred block-type alkylene oxides are -PO$_x$-EO$_y$-, and -EO$_x$-PO$_y$-EO$_z$- wherein x is in the range of 2 to 300, y is in the range of 2 to 300, and z is in the range of 2 to 300.

In a preferred embodiment, block -PO$_x$-EO$_y$- or -EO$_x$-PO$_y$-EO$_z$- copolymers comprising a terminal ethylene oxide block are used, wherein the PO units may be exchanged by another $C_4$ to $C_6$ alkylene oxide.

If copolymers of ethylene oxide (EO) and a further $C_3$ to $C_4$ alkylene oxide are used the EO content may generally be from 3 to 95% by weight. Preferably the EO content is from 5 to 80% by weight, more preferably from 5 to 60% by weight, even more preferably below 50% by weight, even more preferably below 40% by weight, even more preferably from 5 to 40% by weight, even more preferably from 5 to 30% by weight, even more preferably from 6 to 25% by weight, most preferably from 8 to 20% by weight.

Generally, the molecular weight $M_w$ of the suppressing agent may be from about 500 to about 30000 g/mol, preferably 2000 to 15000 g/mol. In one embodiment the molecular weight $M_w$ of the suppressing agent is from about 500 to about 8000 g/mol, most preferably from about 1500 to about 3500 g/mol. In another embodiment the molecular weight $M_w$ of the suppressing agent is from about 5000 to about 20000 g/mol, in particular from about 6000 to about 15000 g/mol.

In a first preferred embodiment a compound of formula I is used in which s is 1, 2 or 3, most preferably 1 or 2; and $R^{S12}$, $R^{S13}$, $R^{S14}$ and $R^{S15}$ are independently selected from a $C_2$ to $C_6$ polyoxyalkylene group $R^{S11}$. Such compounds may be prepared by starting from symmetric dialkylentriamines, trialkylenetetramines, tetraalkylenpentamins, such as but not limited to diethylentriamine, triethylenetetramine, dipropylentriamine, tri propylentetramine, methyl diethylentriamine, dimethyl triethylenetetramine, and the like.

In a second preferred embodiment a compound of formula I is used in which s is 1, 2 or 3, most preferably 1 or 2; $R^{S12}$, $R^{S13}$, $R^{S14}$ are independently selected from a $C_2$ to $C_6$ polyoxyalkylene group $R^{S11}$; and $R^{S15}$ is selected from $X^{S4}$—$N(R^{S11})_2$. In this way, a more branched polyoxyalkylene suppressing agent is received. Such compounds may be prepared by starting from branched amine starters, such as but not limited to tris aminoethyl amine and the like.

In a third preferred embodiment n is 1, 2 or 3, most preferably 1 or 2; $R^{S12}$, $R^{S13}$ and $R^{S14}$ are selected from a $C_2$ to $C_6$ polyoxyalkylene group $R^{S11}$; and $R^{S15}$ is selected from $R^{S40}$, and —$X^{S4}$—$N(R^{S40})_2$. In this way, a linear or branched suppressing agent is received which comprises, besides the polyoxyalkylene side chains, also one or more alkyl-substituents. Such compounds may be prepared by starting from linear amines as described above, wherein the secondary amino group(s) are alkyl substituted, or starting from branched amines in which one or more amine groups are alkyl substituted, such as but not limited to tris alkylaminoethyl amine and the like.

In a fourth preferred embodiment s is 1, 2 or 3, preferably 1 or 2, most preferably 1; $R^{S12}$ is selected from $R^{S11}$; $R^{S13}$ and $R^{S14}$ are selected from $R^{S40}$; and $R^{S15}$ is selected from $R^{S21}$. Such compounds may be prepared by starting from symmetrically alkyl substituted dialkylentriamines or trialkylenetetramines, such as but not limited to N,N-dimethyl diethylenetriamine, N,N,N-trimethyl diethylenetriamine, and the like.

In a fifth preferred embodiment n is 1, 2 or 3, preferably 1 or 2, most preferably 1; and $R^{S13}$ is selected from $R^{S11}$; and at least one of $R^{S12}$ and $R^{S14}$ is selected from $R^{S40}$; and $R^{S15}$ is selected from $R^{S21}$. Such compounds may be prepared by starting from asymmetric dialkylentriamines or trialkylenetetramines, such as but not limited to 1-N-methyl diethylenetriamine, 1,3-N-dimethyl diethylenetriamine, and the like.

Particularly preferred embodiments suppressing agents of formula I are those wherein (a) $X^{S1}$ and $X^{S2}$ are ethanediyl or propanediyl, $R^{S11}$, $R^{S12}$, $R^{S13}$, $R^{S14}$, and $R^{S15}$ are a polyoxyalkylene, particularly an oxyethylene-co-oxypropylene polymer, (b) $X^{S1}$ and $X^{S2}$ are ethanediyl or propanediyl, $R^{S11}$, $R^{S12}$, $R^{S13}$, and $R^{S14}$ are a polyoxyalkylene, particularly a oxyethylene-co-oxypropylene polymer, and $R^{S15}$ is $C_1$ to $C_6$ alkyl or a polyoxyalkylene substituted $C_1$ to $C_6$ alkyl, and (c) $X^{S1}$ and $X^{S2}$ are ethanediyl or propanediyl, $R^{S11}$, $R^{S12}$, $R^{S13}$, and $R^{S14}$ are a polyoxyalkylene, particularly an oxyethylene-co-oxypropylene polymer, and $R^{S15}$ is a $C_1$ to $C_6$ amine which is further substituted by a polyoxyalkylene, particularly oxyethylene-co-oxypropylene polymers.

Levelers

One or more levelers may be present in the tin or tin alloy plating bath.

On class of levelers are linear or branched polyimidazolium compounds comprising the structural unit of formula L1

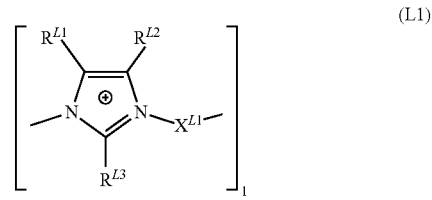

Generally, $R^{L1}$ and $R^{L2}$ may be an H atom or an organic radical having from 1 to 20 carbon atoms. The radicals can be branched or unbranched or comprise functional groups which can, for example, contribute to further crosslinking of the polymeric imidazolium compound. Preferably, $R^{L1}$ and $R^{L2}$ are each, independently of one another, hydrogen atoms or hydrocarbon radicals having from 1 to 6 carbon atoms. Most preferably $R^{L1}$ and $R^{L2}$ are H atoms.

Generally, $R^{L3}$ may be an H atom or an organic radical having from 1 to 20 carbon atoms. Preferably, $R^{L3}$ is an H atom or methyl, ethyl or propyl. Most preferably $R^{L3}$ is an H atom.

Generally, $X^{L1}$ may be a linear, branched or cyclic aliphatic diradical selected from a $C_4$ to $C_{20}$ alkandiyl, which may comprise one or more continuations of the imidazolium compound by branching.

As used herein, "continuation of the polyimidazolium compound by branching" means that the respective spacer group $X^{L1}$ comprises one or more, preferably one or two, groups from which a polyimidazole branch is started. Preferably, $X^{L1}$ does not comprise any continuation of the polyimidazolium compound by branching, i.e. the polyimidazolium compound is a linear polymer.

In a first embodiment $X^{L1}$ is $C_4$ to $C_{14}$ alkanediyl, most preferably $C_4$ to $C_{12}$ alkanediyl, which may be unsubstituted or substituted by $OR^{L4}$, $NR^{L4}_2$, and $S^LR^4$, in which $R^{L4}$ is a $C_1$ to $C_4$ alkyl group. In a particular embodiment, $X^{L1}$ is a pure hydrocarbon radical which does not comprise any functional groups.

Particularly preferred groups $X^{L1}$ are selected from a linear or branched butanediyl, pentanediyl, hexanediyl, heptanediyl, octanediyl, nonanediyl, decanediyl, undecanediyl, and dodecanediyl, which may be unsubstituted or substituted by $OR^{L4}$, $NR^{L4}$. Particularly preferred groups $X^{L1}$ are selected from linear butanediyl, hexanediyl and octanediyl.

In second embodiment, group $X^{L1}$ may be a cyclic alkanediyl of formula

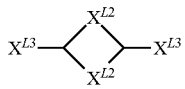

wherein
$X^{L2}$ is independently selected from a $C_1$ to $C_4$ alkandiyl, which may be interrupted by one or two selected from O and $NR^{L4}$, and
$X^{L3}$ is independently selected from (a) a chemical bond or (b) a $C_1$ to $C_4$ alkandiyl, which may be interrupted by O or $NR^{L4}$.
wherein $R^{L4}$ is a $C_1$ to $C_4$ alkyl group.

As used herein, "chemical bond" means that the respective moiety is not present but that the adjacent moieties are bridged so as to form a direct chemical bond between these adjacent moieties. By way of example, if in X—Y—Z the moiety Y is a chemical bond then the adjacent moieties X and Z together form a group X—Z.

Either $X^{L2}$ or $X^{L3}$ or both $X^{L2}$ and $X^{L3}$ may comprise one or more continuations of the imidazolium compound by branching, preferably only $X^2$ may comprise such continuations of the imidazolium compound by branching.

In this second embodiment, most preferably one $X^{L2}$ is selected from methanediyl and the other $X^{L2}$ is selected from propanediyl or both $X^{L2}$ are selected from ethanediyl. Particularly preferred are groups $X^{L1}$ are selected from isophoronediamine, biscyclohexyldiamino methane, and methyl-cyclohexyl-diamine (MDACH).

In a third embodiment, $X^{L1}$ may be a (hetero)arylalkyl diradical selected from $Y^{L2}$—$Y^{L1}$—$Y^{L2}$. Herein $Y^{L1}$ may be a $C_5$ to $C_{20}$ aryl group and $Y^{L2}$ may be independently selected from a linear or branched $C_1$ to $C_6$ alkanediyl. Also here, both, $Y^{L1}$ and $Y^{L2}$ may comprise one or more continuations of the imidazolium compound by branching.

Preferred groups $Y^{L1}$ are selected from phenyl, naphtyl, pyridyl, pyrimidyl, and furanyl, most preferably phenyl. Preferred groups $Y^{L2}$ are selected from a linear or branched $C_1$ to $C_4$ alkanediyl, preferably from methanediyl, ethanediyl, 1,3-propanediyl and 1,4-butanediyl.

The organic radical $X^{L1}$ may comprise not only carbon and hydrogen but also heteroatoms such as oxygen, nitrogen, sulfur or halogens, e.g. in the form of functional groups such as hydroxyl groups, ether groups, amide groups, aromatic heterocycles, primary, secondary, or tertiary amino groups or imino groups.

In particular, the organic radical $X^{L1}$ may be a hydrocarbon diradical which may be substituted or interrupted by functional groups comprising heteroatoms, in particular ether groups. If substituted, it is preferred that $X^{L1}$ does not comprise any hydroxyl groups.

I may generally be an integer from 2 to about 5000, preferably from about 5 to about 3000, even more preferably from about 8 to about 1000, even more preferably from about 10 to about 300, even more preferably from about 15 to about 250, most preferably from about 25 to about 150.

The mass average molecular weight $M_w$ of the additive may generally be from 500 g/mol to 1,000,000 g/mol, preferably from 1000 g/mol to 500,000 g/mol, more preferably from 1500 g/mol to 100,000 g/mol, even more preferably from 2,000 g/mol to 50,000 g/mol, even more preferably from 3,000 g/mol to 40,000 g/mol, most preferably from 5,000 g/mol to 25,000 g/mol.

Preferably the at least one additive comprises a counterion $Y^{o-}$, wherein o is a positive integer selected so that the overall additive is electrically neutral. Preferably o is 1, 2 or 3. Most preferably, the counterion $Y^{o-}$ is selected from chloride, sulfate, methanesulfonate or acetate.

Preferably the number average molecular weight $M_n$ of the polymeric imidazolium compound, determined by gel permeation chromatography, is be greater than 500 g/mol.

Preferably the polymeric imidazolium compound may comprise more than 80% by weight of structural units of the formula L1.

More details and alternatives are described in unpublished European patent application No. 17173987.3, patent publication WO 2016/020216 and International Patent Application No. PCT/EP2017/050054, respectively, which are incorporated herein by reference.

Other suitable leveling agents include, but are not limited to, polyaminoamide and derivatives thereof, polyalkanolamine and derivatives thereof, polyethylene imine and derivatives thereof, quaternized polyethylene imine, polyglycine, poly(allylamine), polyaniline, polyurea, polyacrylamide, poly(melamine-co-formaldehyde), reaction products of amines with epichlorohydrin, reaction products of an amine, epichlorohydrin, and polyalkylene oxide, reaction products of an amine with a polyepoxide, polyvinylpyridine, polyvinylimidazole, polyvinylpyrrolidone, or copolymers thereof, nigrosines, pentamethyl-para-rosaniline hydrohalide, hexamethyl-pararosaniline hydrohalide, or compounds containing a functional group of the formula N—R—S, where R is a substituted alkyl, unsubstituted alkyl, substituted aryl or unsubstituted aryl. Typically, the alkyl groups are $C_1$-$C_6$ alkyl and preferably $C_1$-$C_4$ alkyl. In general, the aryl groups include $C_6$-$C_{20}$ aryl, preferably $C_6$-$C_{12}$ aryl. Such aryl groups may further include heteroatoms, such as sulfur, nitrogen and oxygen. It is preferred that the aryl group is phenyl or napthyl. The compounds containing a functional group of the formula N—R—S are generally known, are generally commercially available and may be used without further purification.

In such compounds containing the N—R—S functional group, the sulfur ("S") and/or the nitrogen ("N") may be attached to such compounds with single or double bonds. When the sulfur is attached to such compounds with a single bond, the sulfur will have another substituent group, such as but not limited to hydrogen, $C_1$-$C_{12}$ alkyl, $C_2$-$C_{12}$ alkenyl, $C_6$-$C_{20}$ aryl, $C_1$-$C_{12}$ alkylthio, $C_2$-$C_{12}$ alkenylthio, $C_6$-$C_{20}$ arylthio and the like. Likewise, the nitrogen will have one or more substituent groups, such as but not limited to hydrogen, $C_1$-$C_{12}$ alkyl, $C_2$-$C_{12}$ alkenyl, $C_7$-$C_{10}$ aryl, and the like. The N—R—S functional group may be acyclic or cyclic. Compounds containing cyclic N—R—S functional groups include those having either the nitrogen or the sulfur or both the nitrogen and the sulfur within the ring system.

Further leveling agents are triethanolamine condensates as described in unpublished international Patent Application No. PCT/EP2009/066581.

In general, the total amount of leveling agents in the electroplating bath is from 0.5 ppm to 10000 ppm based on the total weight of the plating bath. The leveling agents according to the present invention are typically used in a total amount of from about 100 ppm to about 10000 ppm based on the total weight of the plating bath, although greater or lesser amounts may be used.

Grain Refiners

The tin or tin alloy electroplating bath may further contain grain refiners. Grain refiners may be chosen from a compound of formula G1 or G2

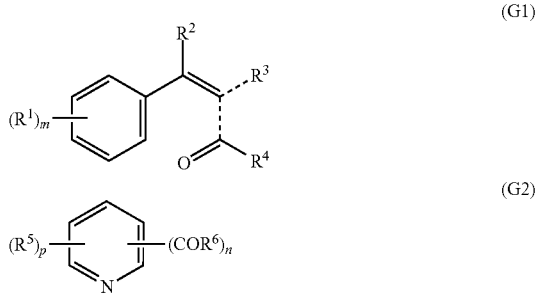

wherein each $R^1$ is independently $C_1$ to $C_6$ alkyl, $C_1$ to $C_6$ alkoxy, hydroxy, or halogen; $R^2$ and $R^3$ are independently selected from H and $C_1$ to $C_6$ alkyl; $R^4$ is H, OH, $C_1$ to $C_6$ alkyl or $C_1$ to $C_6$ alkoxy; m is an integer from 0 to 2; each $R^5$ is independently $C_1$ to $C_6$ alkyl; each $R^6$ is independently chosen from H, OH, $C_1$ to $C_6$ alkyl, or $C_1$ to $C_6$ alkoxy; n is 1 or 2; and p is 0, 1 or 2.

Preferably, each $R^1$ is independently $C_1$ to $C_6$ alkyl, $C_1$ to $C_3$ alkoxy, or hydroxy, and more preferably $C_1$ to $C_4$ alkyl, $C_1$ to $C_2$ alkoxy, or hydroxy. It is preferred that $R^2$ and $R^3$ are independently chosen from H and $C_1$ to $C_3$ alkyl, and more preferably H and methyl. Preferably, $R^4$ is H, OH, $C^1$ to $C^4$ alkyl or $C_1$ to $C_4$ alkoxy, and more preferably H, OH, or $C_1$ to $C_4$ alkyl. It is preferred that $R^5$ is $C_1$ to $C_4$ alkyl, and more preferably $C_1$ to $C_3$ alkyl. Each $R^6$ is preferably chosen from H, OH, or C1 to $C_6$ alkyl, more preferably H, OH, or $C_1$ to $C_3$ alkyl, and yet more preferably H or OH. It is preferred that m is 0 or 1, and more preferably m is 0. Preferably, n is 1. It is preferred that p is 0 or 1, and more preferably p is 0. A mixture of first grain refiners may be used, such as two different grain refiners of formula 1, 2 different grain refiners of formula 2, or a mixture of a grain refiner of formula 1 and a grain refiner of formula 2.

Exemplary compounds useful as such grain refiners include, but are not limited to, cinnamic acid, cinnamaldehyde, benzalacetone, picolinic acid, pyridinedicarboxylic acid, pyridinecarboxaldehyde, pyridinedicarboxaldehyde, or mixtures thereof. Preferred grain refiners include benzalacetone, 4-methoxy benzaldehyde, benzylpyridin-3-carboxylate, and 1,10-phenantroline.

Further grain refiners may be chosen from an α,β-unsaturated aliphatic carbonyl compound. Suitable α,β-unsaturated aliphatic carbonyl compound include, but are not limited to, α,β-unsaturated carboxylic acids, α,β-unsaturated carboxylic acid esters, α,β-unsaturated amides, and α,β-unsaturated aldehydes. Preferably, such grain refiners are chosen from α,β-unsaturated carboxylic acids, α,β-unsaturated carboxylic acid esters, and α,β-unsaturated aldehydes, and more preferably α,β-unsaturated carboxylic acids, and α,β-unsaturated aldehydes. Exemplary α,β-unsaturated aliphatic carbonyl compounds include (meth) acrylic acid, crotonic acid, C to C6 alkyl meth)acrylate, (meth)acrylamide, $C_1$ to $C_6$ alkyl crotonate, crotonamide, crotonaldehyde, (meth)acrolein, or mixtures thereof. Preferred α,β-unsaturated aliphatic carbonyl compounds are (meth)acrylic acid, crotonic acid, crotonaldehyde, (meth) acrylaldehyde or mixtures thereof.

In one embodiment, grain refiners may be present in the plating baths in an amount of 0.0001 to 0.045 g/l. Preferably, the grain refiners are present in an amount of 0.0001 to 0.04 g/l, more preferably in an amount of 0.0001 to 0.035 g/l, and yet more preferably from 0.0001 to 0.03 g/l. Compounds useful as the first grain refiners are generally commercially available from a variety of sources and may be used as is or may be further purified.

In another more preferred embodiment, the compositions for tin or tin alloy electroplating do comprises a single grain refiner, more preferably a single grain refiner that is no α,β-unsaturated aliphatic carbonyl compound, most preferably essentially no grain refiner or no grain refiner at all. Surprisingly, it was found that particularly for filling recessed features having an aperture size below 50 μm there is no need to use any grain refiners but the suppressing agent leads to a good coplanarity without the use of any grain refiner.

The present compositions may optionally include further additives, such as antioxidants, organic solvents, complexing agents, and mixtures thereof.

Antioxidants

Antioxidants may optionally be added to the present composition to assist in keeping the tin in a soluble, divalent state. It is preferred that one or more antioxidants are used in the present compositions. Exemplary antioxidants include, but are not limited to, hydroquinone, and hydroxylated and/or alkoxylated aromatic compounds, including sulfonic acid derivatives of such aromatic compounds, and preferably are: hydroquinone; methylhydroquinone; resorcinol; catechol; 1,2,3-trihydroxybenzene; 1,2-dihydroxybenzene-4-sulfonic acid; 1,2-dihydroxybenzene-3,5-disulfonic acid; 1,4-dihydroxybenzene-2-sulfonic acid; 1,4-dihydroxybenzene-2,5-disulfonic acid; 2,4-dihyroxybenzene sulfonic acid, and p-Methoxyphenol. Such antioxidants are disclosed in U.S. Pat. No. 4,871,429. Other suitable antioxidants or reducing agents include, but are not limited to, vanadium compounds, such as vanadylacetylacetonate, vanadium triacetylacetonate, vanadium halides, vanadium oxyhalides, vanadium alkoxides and vanadyl alkoxides. The concentration of such reducing agent is well known to those skilled in the art, but is typically in the range of from 0.1 to 10 g/l, and preferably from 1 to 5 g/l. Such antioxidants are generally commercially available from a variety of sources.

Electrolyte

In general, as used herein "aqueous" means that the present electroplating compositions comprises a solvent comprising at least 50% of water. Preferably, "aqueous" means that the major part of the composition is water, more preferably 90% of the solvent is water, most preferably the solvent essentially consists of water. Any type of water may be used, such as distilled, deinonized or tap.

Tin

The tin ion source may be any compound capable of releasing metal ions to be deposited in the electroplating bath in sufficient amount, i.e. is at least partially soluble in the electroplating bath. It is preferred that the metal ion source is soluble in the plating bath. Suitable metal ion sources are metal salts and include, but are not limited to, metal sulfates, metal halides, metal acetates, metal nitrates, metal fluoroborates, metal alkylsulfonates, metal arylsulfonates, metal sulfamates, metal gluconates and the like.

The metal ion source may be used in the present invention in any amount that provides sufficient metal ions for electroplating on a substrate. When the metal is solely tin, the tin salt is typically present in an amount in the range of from about 1 to about 300 g/l of plating solution. In a preferred embodiment the plating solution is free of lead, that is, they contain 1 wt % lead, more preferably below 0.5 wt %, and yet more preferably below 0.2 wt %, and still more preferably are free of lead. In another preferred embodiment the plating solution is essentially free of copper, that is, they contain below 1 wt % copper, more preferably below 0.1 wt %, and yet more preferably below 0.01 wt %, and still more preferably are free of copper.

Silver

Besides tin, the plating baths according to the invention contains silver ions and optionally one or more other alloying metal ions. Suitable alloying metals include, without limitation, gold, copper, bismuth, indium, zinc, antimony, manganese and mixtures thereof. Preferred alloying metals are copper, bismuth, indium, and mixtures thereof. Any bath-soluble salt of silver and other alloying metal (together referred to as alloying metal) may suitably be used as the source of alloying silver and other alloy metal ions. Examples of such alloying metal salts include, but are not limited to: metal oxides; metal halides; metal fluoroborate; metal sulfates; metal alkanesulfonates such as metal methanesulfonate, metal ethanesulfonate and metal propanesulfonate; metal arylsulfonates such as metal phenylsulfonate, metal toluenesulfonate, and metal phenolsulfonate; metal carboxylates such as metal gluconate and metal acetate; and the like. Preferred alloying metal salts are metal sulfates; metal alkanesulfonates; and metal arylsulfonates. When silver is added to the present compositions, a binary alloy deposit is achieved. When 2, 3 or more different alloying metals are added to the present compositions, tertiary, quaternary or higher order alloy deposits are achieved. The amount of such alloying metal used in the present compositions will depend upon the particular tin-alloy desired. The selection of such amounts of alloying metals is within the ability of those skilled in the art. It will be appreciated by those skilled in the art that when certain alloying metals besides silver are used, an additional complexing agent besides the complexing agents according to the invention may be required.

The present electroplating compositions are suitable for depositing a tin-silver-containing layer, Exemplary tin-alloy layers include, without limitation, tin-silver-copper, tin-silver-indium, tin-silver-bismuth, tin-silver-copper-antimony, tin-silver-copper-manganese, tin-silver-zinc-copper, and tin-silver-indium-bismuth. Preferably, the present electroplating compositions deposit pure tin-silver, tin-silver-copper, tin-indium, tin-silver-bismuth, tin-silver-indium, and tin-silver-indium-bismuth, and more preferably pure tin-silver.

Silver alloys deposited from the present electroplating bath contain an amount of tin ranging from 0.01 to 99.99 wt %, and an amount of one silver and optionally other alloying metals ranging from 99.99 to 0.01 wt %, based on the weight of the alloy, as measured by either atomic adsorption spectroscopy (AAS), X-ray fluorescence (XRF), inductively coupled plasma mass spectrometry (ICP-MS). Preferably, the tin-silver alloys deposited using the present invention contain from 90 to 99.99 wt % tin and 0.01 to 10 wt % of silver and any other alloying metal. More preferably, the tin-silver alloy deposits contain from 95 to 99.9 wt % tin and 0.1 to 5 wt % of silver and any other alloying metal. Tin-silver alloy is the preferred tin-alloy deposit, and preferably contains from 90 to 99.9 wt % tin and from 10 to 0.1 wt % silver. More preferably, the tin-silver alloy deposits contain from 95 to 99.9 wt % tin and from 5 to 0.1 wt % silver. For many applications, the eutectic composition of an alloy may be used. Alloys deposited according to the present invention are substantially free of lead, that is, they contain 1 wt % lead, more preferably below 0.5 wt %, and yet more preferably below 0.2 wt %, and still more preferably are free of lead.

Bath

In general, besides the metal ion source and at least one of the complexing agents, the present metal electroplating compositions preferably include electrolyte, i. e. acidic or alkaline electrolyte, one or more sources of metal ions, optionally halide ions, and optionally other additives like surfactants and grain refiners. Such baths are typically aqueous. The water may be present in a wide range of amounts. Any type of water may be used, such as distilled, deionized or tap.

Preferably, the plating baths of the invention are acidic, that is, they have a pH below 7. Typically, the pH of the tin or tin alloy electroplating composition is below 4, preferably below 3, most preferably below 2.

The electroplating baths of the present invention may be prepared by combining the components in any order. It is preferred that the inorganic components such as metal salts, water, electrolyte, are first added to the bath vessel followed by the organic components such as surfactants, grain refiners, levelers and the like.

Typically, the plating baths of the present invention may be used at any temperature from 10 to 65 degrees C. or higher. It is preferred that the temperature of the plating baths is from 10 to 35 degrees C. and more preferably from 15 degrees to 30 degrees C.

Suitable electrolytes include such as, but not limited to, sulfuric acid, acetic acid, fluoroboric acid, alkylsulfonic acids such as methanesulfonic acid, ethanesulfonic acid, propanesulfonic acid and trifluoromethane sulfonic acid, arylsulfonic acids such as phenyl sulfonic acid and toluenesulfonic acid, sulfamic acid, hydrochloric acid, phosphoric acid, tetraalkylammonium hydroxide, preferably tetramethylammonium hydroxide, sodium hydroxide, potassium hydroxide and the like. Acids are typically present in an amount in the range of from about 1 to about 300 g/l.

In one embodiment the at least one additive comprises a counterion $Y^{o-}$ selected from methane sulfonate, sulfate or acetate. wherein o is a positive integer.

Application

The plating compositions of the present invention are useful in various plating methods where a tin-containing layer is desired, and particularly for depositing a tin-containing solder layer on a semiconductor wafer comprising a plurality of conductive bonding features. Plating methods include, but are not limited to, horizontal or vertical wafer plating, barrel plating, rack plating, high speed plating such as reel-to-reel and jet plating, and reckless plating, and preferably horizontal or vertical wafer plating. A wide variety of substrates may be plated with a tin-containing deposit according to the present invention. Substrates to be plated are conductive and may comprise copper, copper alloys, nickel, nickel alloys, nickel-iron containing materials. Such substrates may be in the form of electronic components such as (a) lead frames, connectors, chip capacitors, chip resistors, and semiconductor packages, (b) plastics such as circuit boards, and (c) semiconductor wafers. Preferably the substrates are semiconductor wafers. Accordingly, the present invention also provides a method of depositing a tin-containing layer on a semiconductor wafer comprising: providing a semiconductor wafer comprising a plurality of conductive bonding features; contacting the semiconductor wafer with the composition described above; and applying sufficient current density to deposit a tin-containing layer on the conductive bonding features. Preferably, the bonding features comprise copper, which may be in the form of a pure copper layer, a copper alloy layer, or any interconnect structure comprising copper. Copper pillars are one preferred conductive bonding feature. Optionally, the copper pillars may comprise a top metal layer, such as a nickel layer. When the conductive bonding features have a top metal layer, then the pure tin solder layer is deposited on the top metal layer of the bonding feature. Conductive bonding features, such as bonding pads, copper pillars, and the like, are well-known in the art, such as described in U.S. Pat. No. 7,781,325, US 2008/0054459 A, US 2008/0296761 A, and US 2006/0094226 A.

Process

In general, when the present invention is used to deposit tin alloys on a substrate the plating baths are agitated during use. Any suitable agitation method may be used with the present invention and such methods are well-known in the art. Suitable agitation methods include, but are not limited to, inert gas or air sparging, work piece agitation, impingement and the like. Such methods are known to those skilled in the art. When the present invention is used to plate an integrated circuit substrate, such as a wafer, the wafer may be rotated such as from 1 to 150 RPM and the plating solution contacts the rotating wafer, such as by pumping or spraying. In the alternative, the wafer need not be rotated where the flow of the plating bath is sufficient to provide the desired metal deposit.

The tin alloy is deposited in recesses according to the present invention without substantially forming voids within the metal deposit. By the term "without substantially forming voids", it is meant that there are no voids in the metal deposit which are bigger than 1000 nm, preferably 500 nm, most preferably 100 nm.

Plating equipment for plating semiconductor substrates are well known. Plating equipment comprises an electroplating tank which holds tin or tin alloy electrolyte and which is made of a suitable material such as plastic or other material inert to the electrolytic plating solution. The tank may be cylindrical, especially for wafer plating. A cathode is horizontally disposed at the upper part of tank and may be any type substrate such as a silicon wafer having openings.

These additives can be used with soluble and insoluble anodes in the presence or absence of a membrane or membranes separating the catholyte from the anolyte.

The cathode substrate and anode are electrically connected by wiring and, respectively, to a power supply. The cathode substrate for direct or pulse current has a net negative charge so that the metal ions in the solution are reduced at the cathode substrate forming plated metal on the cathode surface. An oxidation reaction takes place at the anode. The cathode and anode may be horizontally or vertically disposed in the tank.

In general, when preparing tin alloy bumps, a photoresist layer is applied to a semiconductor wafer, followed by standard photolithographic exposure and development techniques to form a patterned photoresist layer (or plating mask) having openings or vias therein. The dimensions of the plating mask (thickness of the plating mask and the size of the openings in the pattern) defines the size and location of the tin or tin alloy layer deposited over the I/O pad and UBM. The diameter of such deposits typically range from 1 to 300 μm, preferably in the range from 2 to 100 μm.

All percent, ppm or comparable values refer to the weight with respect to the total weight of the respective composition except where otherwise indicated. All cited documents are incorporated herein by reference.

The following examples shall further illustrate the present invention without restricting the scope of this invention.

EXAMPLES

Example 1

Preparation of Complexing Agents

Example 1.1

1,8-Bis(2-pyridyl)-3,6-dithiaoctane

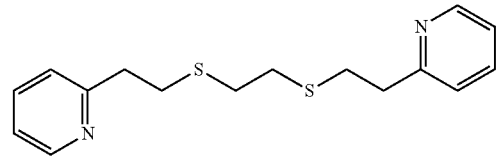 [SMILES: c1ccc(CCSCCSCCc2ccccn2)nc1]

To a solution of 346.8 g 2-vinylpyridine in 200 ml iso-propanol were added at 50° C. 153.8 g of 1,2-ethanedithiol under inert atmosphere. Then the reaction mixture was heated to reflux. After 7 hours of stirring at reflux the temperature was reduced to 60° C. The warm solution was then stirred into 1000 ml of 10° C. cold petroleum ether. The precipitate was filtered off and dried in vacuo at 35° C. to yield 417.3 g of 1,8-bis(2-pyridyl)-3,6-dithiaoctane as a colourless solid (mp. 48.9-49.4° C.; assay by GC 99.5%).

Example 1.2

1,9-Bis-(3-pyridyl)-2,5,8-trithianonane

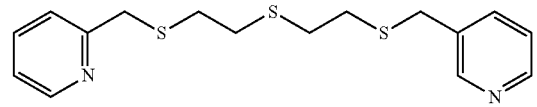 [SMILES: c1ccc(CSCCSCCSCc2cccnc2)nc1]

Under inert atmosphere 14.3 g of a 21% solution of sodium ethylate in ethanol were put into 20 ml of dry ethanol at 0 to 5° C. Then 1.71 g of bis-(2-mercaptoethyl)-sulfide were added at 0 to 4° C. followed by the addition of a solution of 5.20 g 3-(bromomethyl)-pyridine hydrobromide in 50 ml of ethanol and three drops of water at −8 to 4° C. After stirring overnight at room temperature the reaction mixture was concentrated in vacuo. The residue was diluted with 30 ml of dichloromethane and extracted with 30 ml of water. The aqueous phase was extracted again four times each with 30 ml of dichloromethane and the collected organic phases were dried over sodium sulfate. After filtration and concentration in vacuo the crude product was purified by chromatography over silica gel with cyclohexane and ethyl acetate as the eluents (eluation with a gradient) to yield 2.3 g of 1,9-bis-(3-pyridyl)-2,5,8-trithia-nonane as a light yellow oil (mp 55.3° C.-55.6° C., assay by C-NMR>95%).

Example 1.3

1,13-Bis(2-pyridyl)-2,5,9,12-tetrathiatridecane

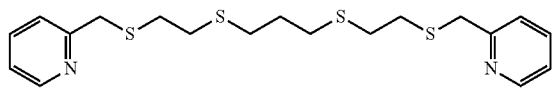 [SMILES: c1ccc(CSCCSCCCSCCSCc2ccccn2)nc1]

Under inert atmosphere 14.3 g of a 21% solution of sodium ethylate in ethanol were put into 20 ml of dry ethanol at 0 to 5° C. Then 1.94 ml of 3,7-dithia-nonane-1,9-dithiol were added at 0 to 4° C. followed by the addition of a solution of 3.28 g 2-(chloromethyl)-pyridine hydrochloride in 50 ml of dry ethanol at −8 to 4° C. After stirring overnight at room temperature the reaction mixture was concentrated in vacuo. The residue was diluted with 50 ml of dichloromethane and extracted with 50 ml of water. The aqueous phase was extracted again three times each with 50 ml of dichloromethane and the collected organic phases were dried over sodium sulfate. After filtration and concentration in vacuo 3.81 g of 1,9-bis-(2-pyridyl)-2,5,9,12-tetrathiadodecane were obtained as a brownish oil (assay by C-NMR>95%).

Example 1.4

(2R,3R)-1,4-bis[2-(2-pyridyl)ethylsulfanyl]butane-2,3-diol/(2S,3S)-1,4-bis[2-(2-pyridyl)-ethylsulfanyl]butane-2,3-diol

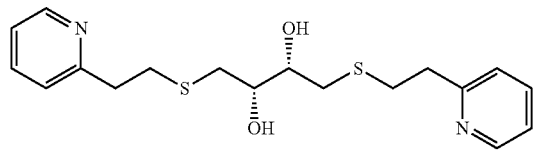

To a solution of 1.54 g DL-dithiothreitol in 50 ml ethanol were added 2.17 g 2-vinylpyridine and the reaction mixture was heated to reflux for 7 hours. The reaction mixture was then stirred overnight at room temperature. After that the reaction mixture was concentrated in vacuo to yield 3.7 g of 1,4-bis[2-(2-pyridyl)ethylsulfanyl]butane-2,3-diol (DL) as a viscous oil, which solidifies when cooling to room temperature (mp. 92.8-93.4° C. assay by C-NMR>95%).

Example 1.5

1,6-Bis(2-methylpyridyl)-meso-dithioerythritol

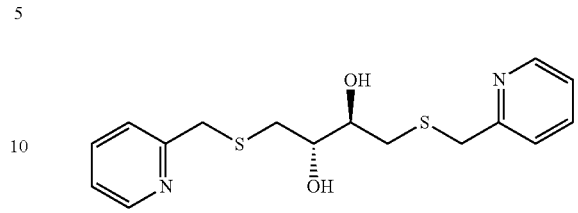

To a solution of 14.30 g of a 21% solution of sodium ethylate in 20 ml of dry ethanol were added 1.54 g of meso-dithioerythritol at 0 to 5° C. within 10 minutes under inert atmosphere. Then a solution of 3.28 g 2-(chloromethyl)-pyridine hydrochloride in 50 ml of dry ethanol was added at −5 to 5° C. When the addition was finished the reaction mixture was let to come to room temperature, stirred overnight at room temperature and concentrated in vacuo. The residue was diluted with 50 ml of dichloromethane and extracted with 50 ml of water. The aqueous phase was extracted again three times each with 50 ml of dichloromethane and the collected organic phases were dried over sodium sulfate. After filtration and concentration in vacuo 3.5 g of 1,6-bis(2-methylpyridyl)-meso-dithioerythritol were obtained as a beige solid (mp. 101.5-102.3° C.; assay by C-NMR 90-95%).

Example 1.6

1,11-Bis(2-pyridyl)-6-oxa-3,9-dithiaundecane

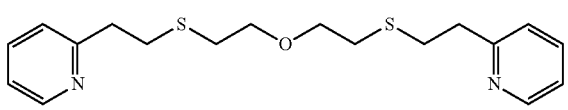 [SMILES: c1ccc(CCSCCOCCSCCc2ccccn2)nc1]

To a solution of 173.4 g 2-vinylpyridine in 170 ml iso-propanol 116.4 g di-(2-mercaptoethyl)-ether were added under inert atmosphere. Then the reaction mixture was heated to reflux. After stirring for 7 hours at reflux the reaction mixture was cooled to room temperature and concentrated in vacuo. The crude product was then washed three times with 150 ml petrolether each time to yield 289.9 g of 1,11-bis(2-pyridyl)-6-oxa-3,9-dithiaundecane as a brownish viscous oil (assay by GC 97.6%).

Example 1.7

1,8-Bis(4-pyridyl)-3,6-dithiaoctane

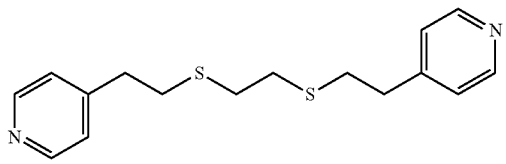 [SMILES: c1cc(CCSCCSCCc2ccncc2)ccn1]

To a solution of 9.42 g of 1,2-ethanedithiol in 40 ml iso-propanol were added 21.68 g 4-vinylpyridine under inert atmosphere. Then the reaction mixture was heated to reflux. After stirring overnight at reflux the temperature was reduced to room temperature and the reaction mixture was concentrated in vacuo. Then the residue was stirred into 150 ml of petroleum ether. The precipitate was filtered off and dried in vacuo at 35° C. to yield 30.3 g of 1,8-bis(4-pyridyl)-3,6-dithiaoctane as a beige solid (mp. 69.5-70° C.; assay by GC 99.5%).

Example 1.8

1,14-Bis(2-pyridyl)-6,9-dioxa-3,12-dithiatetradecane

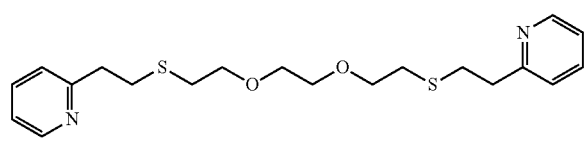 [SMILES: c1ccc(CCSCCOCCOCCSCCc2ccccn2)nc1]

To a solution of 173.4 g 2-vinylpyridine in 170 ml iso-propanol 153.5 g 3,6-dioxa-1,8-octane-dithiol were added under inert atmosphere. Then the reaction mixture was heated to reflux. After stirring for 7 hours at reflux the reaction mixture was cooled to room temperature, concentrated in vacuo, washed three times each with 100 ml petroleum ether and concentrated again in vacuo to yield 310.33 g of 1,14-Bis(2-pyridyl)-6,9-dioxa-3,12-dithiatetradecane as a brownish viscous oil (assay by GC 96.4%).

Example 1.9

1,15-Bis(4-pyridyl)-3,6,10,13-tetrathiapentadecane

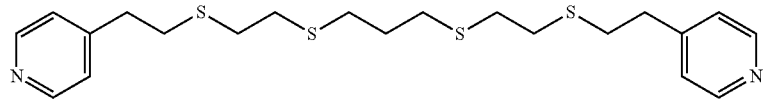 [SMILES: c1cc(CCSCCSCCCSCCSCCc2ccncc2)ccn1]

To a solution of 2.17 g 4-vinylpyridine in 50 ml iso-propanol were added 2.28 g 3,7-dithia-nonane-1,9-dithiol. Then the reaction mixture was heated to reflux. After stirring 8.5 h at reflux the reaction mixture was cooled to room temperature and concentrated in vacuo. The oily residue was purified by chromatography on silica gel with dichloromethane/methanol as the eluents (elution with a gradient) to yield 3.4 g of 1,15-bis(4-pyridyl)-3,6,10,13-tetrathiapentadecane as a colourless solid (mp. 54.5-56.2° C.; assay by C-NMR>95%).

Example 1.10

(2R,3S)-1,4-bis[2-(4-pyridyl)ethylsulfanyl]butane-2,3-diol

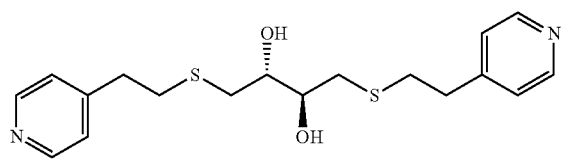 [SMILES: O[C@H](CSCCc1ccncc1)[C@@H](O)CSCCc1ccncc1]

To a solution of 177.1 g 4-vinylpyridine in 170 ml iso-propanol were added 124.7 g meso-dithioerythritol. Then the reaction mixture was heated to reflux. After stirring 7 hours at reflux the reaction mixture was cooled to 50° C. and then fed into 1500 ml 15° C. cold water. The precipitate was filtered off and dried in vacuo at 60° C. to yield 284.4 g of (2R,3S)-1,4-bis[2-(4-pyridyl)ethylsulfanyl]butane-2,3-diol as a white powder (mp. 119.4-120.8° C.; assay by GC 98.7%).

Example 1.11

1-[2-[2-(2-imidazol-1-ylethylsulfanyl)ethylsulfanyl]ethyl]imidazole

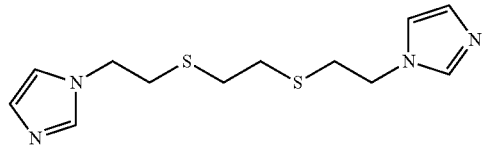 [SMILES: c1cn(CCSCCSCCn2ccnc2)cn1]

Under inert atmosphere 79.8 g KOH were dissolved in 1200 ml ethanol. Then 25.9 g 1,2-ethanethiol were added. After stirring 1 hour at room temperature 94.7 g 1-(2-chloroethyl)-imidazole hydrochloride were added. The reaction mixture was heated up and stirred for 5.5 hours at 60° C. While cooling down to room temperature the reaction mixture was stirred overnight. After concentration in vacuo the residue was diluted with 250 ml dichloromethane and extracted with 250 ml of water. The aqueous phase was extracted again three times each with 250 ml dichloromethane and the collected organic phases were dried over sodium sulfate. After filtration and concentration in vacuo the crude product was purified by chromatography over silica gel with dichloromethane and methanol as the eluents (eluation with a gradient) to yield 49.5 g of 1-[2-[2-(2-imidazol-1-ylethylsulfanyl)ethylsulfanyl]ethyl]imidazole as a beige solid (mp. 44.4-46.0° C.; assay by C-NMR>95%).

Example 1.12

1-methyl-2-[2-[2-[2-(1-methylpyridin-1-ium-2-yl)ethylsulfanyl]ethylsulfanyl]ethyl] pyridin-1-ium; methyl sulfate

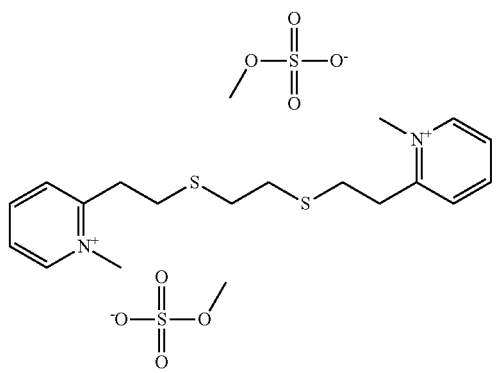

To a solution of 4.56 g 1,8-Bis(2-pyridyl)-3,6-dithiooctane in 20 ml acetonitrile was added 2.84 ml dimethyl sulfate. The reaction mixture was then stirred at 45° C. for 27 h and stirring was continued overnight at room temperature. The reaction mixture was concentrated in vacuo to yield 8.4 g of 1-methyl-2-[2-[2-[2-(1-methylpyridin-1-ium-2-yl)ethylsulfanyl]ethylsulfanyl]ethyl] pyridin-1-ium; methyl sulfate as a viscous oil, which solidified while standing (mp. 46.4-47.9° C. assay by C-NMR>95%).

Example 1.13

1,13-Bis(3-pyridyl)-2,5,9,12-tetrathiatridecane

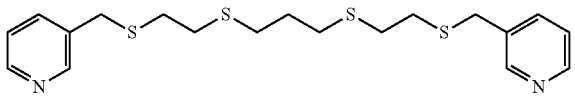 [SMILES: c1cncc(CSCCSCCCSCCSCc2cccnc2)c1]

Under inert atmosphere 14.3 g of a 21% solution of sodium ethylate in ethanol were put into 20 ml of dry ethanol at 0 to 5° C. Then 1.94 ml of 3,7-dithia-nonane-1,9-dithiol were added at −4 to 4° C. followed by the addition of a solution of 5.06 g 3-(bromomethyl)-pyridine hydrobromide in 75 ml of ethanol at −4 to 5° C. After stirring overnight at room temperature the reaction mixture was concentrated in vacuo. The residue was diluted with 50 ml of dichloromethane and extracted with 50 ml of water. The aqueous phase was extracted again three times each with 50 ml of dichloromethane and the collected organic phases were dried over sodium sulfate. After filtration and concentration in vacuo the crude product was purified by chromatography over silica gel with dichloromethane and methanol as the eluents (eluation with a gradient) to yield 2.26 g of 1,13-Bis(3-pyridyl)-2,5,9,12-tetrathiatridecane as a yellowish oil (assay by C-NMR>95%).

Example 1.14

1,13-Bis(4-pyridyl)-2,5,9,12-tetrathiatridecane

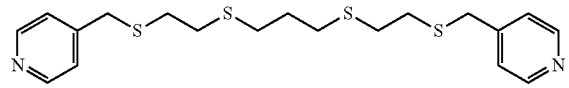 [SMILES: c1cc(CSCCSCCCSCCSCc2ccncc2)ccn1]

Under inert atmosphere 14.3 g of a 21% solution of sodium ethylate in ethanol were put into 20 ml of dry ethanol at 0 to 5° C. Then 1.94 ml of 3,7-dithia-nonane-1,9-dithiol were added at −4 to 4° C. followed by the addition of a solution of 3.28 g 4-(chloromethyl)-pyridine hydrochloride in 50 ml of ethanol with three drops of water at 0 to 4° C. After stirring overnight at room temperature the reaction mixture was concentrated in vacuo. The residue was diluted with 50 ml of dichloromethane and extracted with 30 ml of water. The aqueous phase was extracted again three times each with 50 ml of dichloromethane and the collected organic phases were dried over sodium sulfate. After filtration and concentration in vacuo the crude product was purified by chromatography over silica gel with dichloromethane and methanol as the eluents (eluation with a gradient) to yield 2.40 g of 1,13-bis(4-pyridyl)-2,5,9,12-tetrathiatridecane as a yellowish oil (assay by C-NMR>95%).

Example 1.15

1-[3-[2-[2-(3-imidazol-1-ylpropylsulfanyl)ethylsulfanyl]ethylsulfanyl]propyl]-imidazole

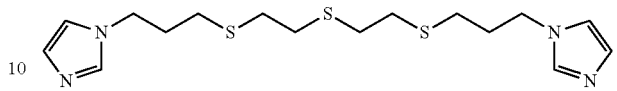

To a solution of 2.21 ml 1-allylimidazole in 20 ml of iso-propanol were added 1.31 g 2,2'-thiodi-ethanethiol and 164 mg AIBN. Then the reaction mixture was heated to reflux. After stirring 5 hours at reflux the reaction mixture was cooled to room temperature and stirred overnight. After concentration in vacuo the oily residue was purified by chromatography on silica gel with dichloromethane/methanol as the eluents (eluation with a gradient) to yield 1.1 g of 1-[3-[2-[2-(3-imidazol-1-ylpropylsulfanyl)ethylsulfanyl]ethylsulfanyl]propyl]imidazole as a colourless oil. (assay by C-NMR 80-90%).

Example 1.16

(2S,3R)-1,4-bis(3-imidazol-1-ylpropylsulfanyl)butane-2,3-diol

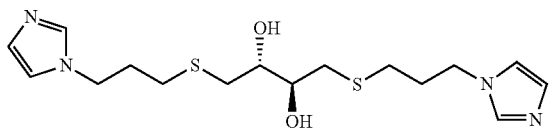 [SMILES: O[C@H](CSCCCn1ccnc1)[C@@H](O)CSCCCn1ccnc1]

To a solution of 2.21 ml 1-allylimidazole in 20 ml iso-propanol were added 1.56 g meso-dithio-erythritol and 164 mg AIBN. Then the reaction mixture was heated to reflux. After stirring 4.5 hours at reflux another 164 mg AIBN were added and the stirring was continued overnight at reflux. Then 164 mg AIBN were added and after 4 hours of stirring at reflux another 164 mg AIBN. After stirring 4 more hours at reflux the reaction mixture was let to cool to room temperature while stirring overnight. After concentration in vacuo the crude product was purified by chromatography over silica gel with dichloromethane and methanol as the eluents (eluation with a gradient) to yield 1.7 g of (2S,3R)-1,4-bis(3-imidazol-1-ylpropylsulfanyl)butane-2,3-diol as a slightly yellowish oil. (assay by C-NMR 85-90%).

Example 1.17

(2R,3S)-1,4-bis(2-morpholinoethylsulfanyl)butane-2,3-diol

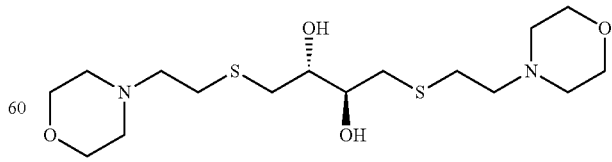

Under inert atmosphere 14.3 g of a 21% solution of sodium ethylate in ethanol were put into 20 ml of dry ethanol at 0 to 5° C. Then 1.54 g meso-dithioerythritol were added at 0 to 4° C. followed by the addition of a solution of 3.72 g 4-(2-chloroethyl)morpholine hydrochloride in 50 ml of dry ethanol at −7 to 4° C. After stirring overnight at room temperature the reaction mixture was concentrated in vacuo. The residue was diluted with 50 ml dichloromethane and extracted with 50 ml of water. The aqueous phase was extracted again four times with dichloromethane and the collected organic phases were dried over sodium sulfate. After filtration and concentration in vacuo the crude product was purified by chromatography over silica gel with dichloromethane and methanol as the eluents (eluation with a gradient) and 1.9 g of (2R,3S)-1,4-bis(2-morpholinoethylsulfanyl)butane-2,3-diol were obtained as a slightly yellowish solid (mp. 88.0-89.1° C.; assay by C-NMR>95%).

To a solution of 1.56 g meso-dithioerythritol in 20 ml iso-propanol were added under inert atmosphere 2.18 ml 1-vinylpyrrolidone. Then the reaction mixture was heated to reflux. After stirring 6 hours at reflux the stirring was continued overnight at room temperature. After concentration in vacuo the crude product was purified by chromatography over silica gel with dichloromethane and methanol as the eluents (eluation with a gradient) to yield 2.6 g of 1-[2-[(2R,3S)-2,3-dihydroxy-4-[2-(2-oxopyrrolidin-1-yl) ethylsulfanyl]butyl]sulfanylethyl]pyrrolidin-2-one as a white solid (mp. 104.1-106.0° C.; assay by C-NMR>95%).

Example 1.20

2,2-bis[3-[2-(2-pyridyl)ethylsulfanyl]propoxymethyl]butan-1-ol

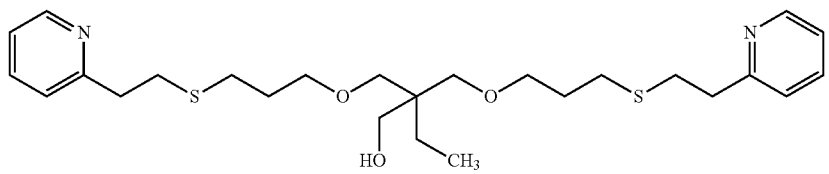

Example 1.18

(2R,3S)-1,4-bis(2-imidazol-1-ylethylsulfanyl)butane-2,3-diol

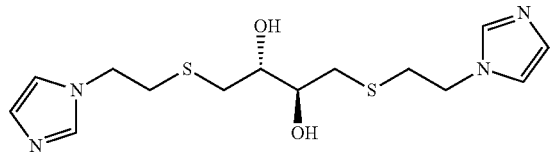 [SMILES: O[C@H](CSCCn1ccnc1)[C@@H](O)CSCCn1ccnc1]

To a solution of 1.56 g meso-dithioerythritol in 20 ml iso-propanol were added under inert atmosphere 1.85 ml 1-vinylimidazol and 164 mg AIBN. Then the reaction mixture was heated to reflux. After stirring 6 hours at reflux the stirring was continued overnight at room temperature. The precipitated product was filtered off, washed with petroleum ether and dried in vacuo to yield 2.66 g of (2R,3S)-1,4-bis (2-imidazol-1-ylethylsulfanyl)butane-2,3-diol as a slightly yellow solid (mp. 135.4-140.8° C.; assay by C-NMR 85-90%).

Example 1.19

1-[2-[(2R,3S)-2,3-dihydroxy-4-[2-(2-oxopyrrolidin-1-yl)ethylsulfanyl]butyl]sulfanyl-ethyl]pyrrolidin-2-one

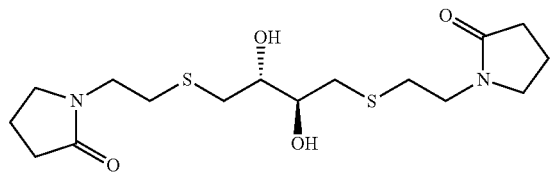 [SMILES: O=C1CCCN1CCSC[C@@H](O)[C@@H](O)CSCCN1CCCC1=O]

To a solution of 1 g 2,2-bis(3-sulfanylpropoxymethyl) butan-1-ol in 20 ml iso-propanol were added 0.79 ml 2-vinylpyridine. After stirring 7 hours at reflux the reaction mixture was cooled to room temperature and stirred overnight. After concentration in vacuo the oily residue was purified by chromatography on silica gel with dichloromethane/methanol as the eluents (eluation with a gradient) to yield 0.9 g of 2,2-bis[3-[2-(2-pyridyl)ethylsulfanyl] propoxymethyl]butan-1-ol as a colourless oil (assay by C-NMR>95%).

Starting Material of Example 20

2,2-bis(3-sulfanyl propoxymethyl)butan-1-ol

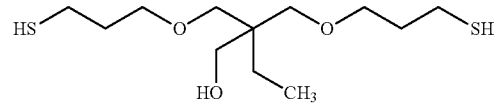

0.12 g AIBN and 5.15 ml thioacetic acid were added to 6.49 g trimethylolpropane-diallylether at room temperature and the reaction mixture was stirred overnight at 70° C. The reaction mixture was then stirred overnight at room temperature. After that excess of thioacetic acid was evaporated in vacuo. Next, 100 ml methanol and 12 ml concentrated hydrochloric acid were added and the reaction was heated to reflux for 3 hours. Then, methanol was removed under vacuum. The residue was diluted with 50 ml water and 50 ml dichloromethane. The aqueous phase was extracted three times with 50 ml of dichloromethane and the collected organic phases were dried over sodium sulfate. After filtration and concentration in vacuo the crude product was purified by chromatography over silica gel with dichloromethane as the eluent (eluation with a gradient) and 1,6 g of 2,2-bis(3-sulfanylpropoxymethyl)butan-1-ol were obtained as a yellowish oil (assay by C-NMR>90%).

Example 1.21

1-[2-[2-[2-(2-imidazol-1-ylethylsulfanyl)ethylsulfanyl]ethylsulfanyl]ethyl]imidazole

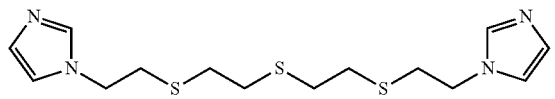 [SMILES: c1cn(CCSCCSCCSCCn2ccnc2)cn1]

To a solution of 33.8 g 2,2'-thiodiethanethiol in 100 ml iso-propanol were added under inert atmosphere 41.29 g 1-vinylimidazol and 0.49 mg AIBN. Then the reaction mixture was heated to reflux. After stirring 6 hours at reflux the stirring was continued overnight at room temperature. After concentration in vacuo the crude product was purified by chromatography over silica gel with dichloromethane/methanol as the eluent (eluation with a gradient) to yield 54 g of 1-[2-[2-[2-(2-imidazol-1-ylethylsulfanyl)ethylsulfanyl]ethylsulfanyl]ethyl]imidazole as a yellow oil (assay by C-NMR>90%).

Example 1.22

1,10-Bis(2-pyridyl)-3,8-dithiadecane

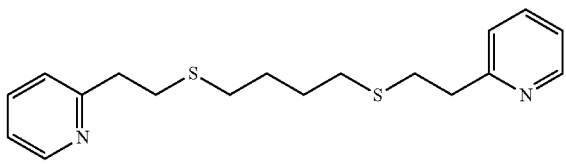 [SMILES: c1ccc(CCSCCCCSCCc2ccccn2)nc1]

To a solution of 2.33 ml 1,4-butanedithiol in 25 ml iso-propanol were added 4.44 ml 2-vinylpyridine. After stirring 7 hours at reflux the reaction mixture was cooled to room temperature and stirred overnight. After concentration in vacuo the residue was purified by chromatography on silica gel with dichloromethane/methanol as the eluents (eluation with a gradient) to yield 5.3 g of 1,10-Bis(2-pyridyl)-3,8-dithiadecane as a yellowish oil. (assay by C-NMR>95%).

Example 1.23

(2R,3S)-1,4-bis(2-pyrazin-2-ylethylsulfanyl)butane-2,3-diol

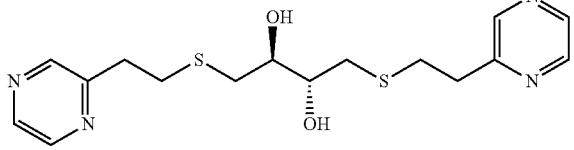

5.15 ml of a 21% solution of sodium ethylate in ethanol were put into a solution of 1.54 g meso-dithioerythritol in ethanol. After stirring 30 min at room temperature 2.08 ml 2-vinylpyrazine were added and the reaction mixture was stirred overnight at room temperature. After concentration in vacuo the crude product was purified by chromatography over silica gel with dichloromethane and methanol as the eluents (eluation with a gradient) and 2.3 g of (2R,3S)-1,4-bis(2-pyrazin-2-ylethylsulfanyl)butane-2,3-diol were obtained as a yellow solid (assay by C-NMR>95%).

Example 1.24

(2R,3S)-1,4-bis(2-thiazol-2-ylpropylsulfanyl)butane-2,3-diol

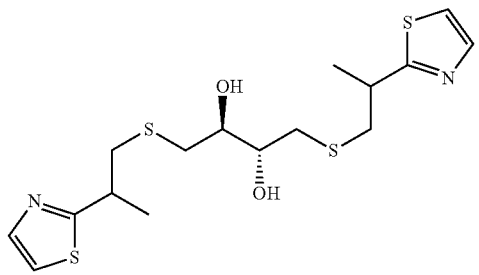 [SMILES: CC(CSC[C@@H](O)[C@@H](O)CSCC(C)c1nccs1)c1nccs1]

To a solution of 1.54 ml meso-dithioerythritol in 20 ml iso-propanol were added 2.37 ml 2-isopropenyl thiazole. After stirring 7.5 hours at reflux the reaction mixture was cooled to room temperature and stirred overnight. After concentration in vacuo the residue was purified by chromatography on silica gel with dichloromethane/methanol as the eluents (eluation with a gradient) to yield 1.2 g of (2R,3S)-1,4-bis(2-thiazol-2-ylpropylsulfanyl)butane-2,3-diol as a red oil (assay by C-NMR>95%).

Example 1.25

3-[2-(2-pyridyl)ethyl]-5-[2-(2-pyridyl)ethylsulfanyl]-1,3,4-thiadiazole-2-thione

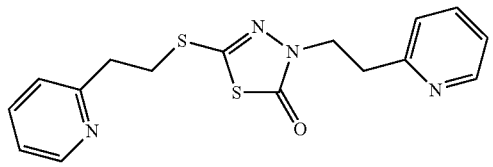 [SMILES: O=c1sc(SCCc2ccccn2)nn1CCc1ccccn1]

To a solution of 1.53 ml 1,3,4-thiadiazole-2,5-dithiol in 20 ml iso-propanol were added 2.22 ml 2-vinylpyridine and further 60 ml iso-propanol. After stirring 7.5 hours at reflux the reaction mixture was cooled to room temperature and stirred overnight. After concentration in vacuo the residue was purified by chromatography on silica gel with dichloromethane/methanol as the eluents (eluation with a gradient) to yield 2.4 g of 3-[2-(2-pyridyl)ethyl]-5-[2-(2-pyridyl)ethylsulfanyl]-1,3,4-thiadiazole-2-thione as a yellow oil (assay by C-NMR>90%).

Example 1.26

2,3-bis[2-(2-pyridyl)ethylsulfanyl]propan-1-ol

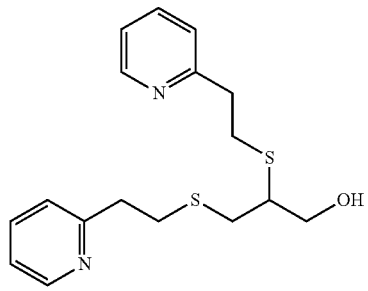 [SMILES: OCC(CSCCc1ccccn1)SCCc1ccccn1]

To a solution of 1.27 ml 2,3-dimercaptopropanol in 25 ml iso-propanol were added 2.17 ml 2-vinylpyridine. After stirring 7 hours at reflux the reaction mixture was cooled to room temperature and stirred overnight. After concentration in vacuo the residue was purified by chromatography on silica gel with dichloromethane/methanol as the eluents (eluation with a gradient) to yield 2.4 g of 2,3-bis[2-(2-pyridyl)ethylsulfanyl]propan-1-ol as a yellow oil (assay by C-NMR>95%).

Example 1.27

6,8-bis[2-(2-pyridyl)ethylsulfanyl]octanoic acid

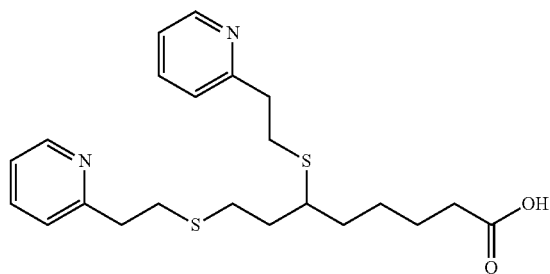 [SMILES: O=C(O)CCCCC(CCSCCc1ccccn1)SCCc1ccccn1]

To a solution of 1 g DL-6,8-thiociticacid in 20 ml iso-propanol were added 1.05 ml 2-vinylpyridine. After stirring 7 hours at reflux the reaction mixture was cooled to room temperature and stirred overnight. After concentration in vacuo the residue was purified by chromatography on silica gel with dichloromethane/methanol as the eluents (eluation with a gradient) to yield 1.1 g of 6,8-bis[2-(2-pyridyl)ethylsulfanyl]octanoic acid as a yellow oil (assay by C-NMR>95%).

Example 1.28

2-[2-[[5-[2-(2-pyridyl)ethylsulfanylmethyl]-1,4-dithian-2-yl]methylsulfanyl]-ethyl]pyridine

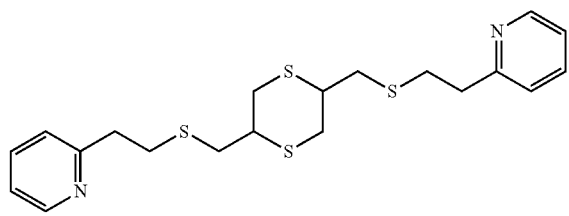 [SMILES: c1ccc(CCSCC2CSC(CSCCc3ccccn3)CS2)nc1]

To a solution of 2.21 g 1,4-dithiane-2,5-di(methanethiol) in 25 ml iso-propanol were added 2.22 ml 2-vinylpyridine. After stirring 7 hours at reflux the reaction mixture was cooled to room temperature and stirred overnight. After concentration in vacuo the residue was purified by chromatography on silica gel with dichloromethane/methanol as the eluents (eluation with a gradient) to yield 3.1 g of 2-[2-[[5-[2-(2-pyridyl)ethylsulfanylmethyl]-1,4-dithian-2-yl]methylsulfanyl]ethyl]pyridine as a coluorless oil (assay by C-NMR 90-95%).

Example 1.29

4,6-bis[2-(2-pyridyl)ethylsulfanyl]-1,3,5-triazin-2-amine

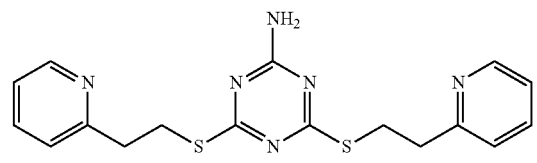 [SMILES: Nc1nc(SCCc2ccccn2)nc(SCCc2ccccn2)n1]

To a solution of 1.78 g 2-amino-1,3,5-triazine-4,6-dithiol in 25 ml DMF were added 2.22 ml 2-vinylpyridine. After stirring 7.5 hours at 86° C. the reaction mixture was cooled to room temperature and stirred overnight. After concentration in vacuo the residue was purified by chromatography on silica gel with dichloromethane/methanol as the eluents (eluation with a gradient) to yield 2.4 g of 4,6-bis[2-(2-pyridyl)ethylsulfanyl]-1,3,5-triazin-2-amine as a brownish oil (assay by C-NMR>95%).

Example 1.30

3-[2-[2-[(2S,3R)-2,3-dihydroxy-4-[2-[1-(3-sulfonatopropyl)pyridine-1-ium-2-yl]ethylsulfanyl]butyl]sulfanylethyl]pyridine-1-ium-1-yl]propane-1-sulfonate

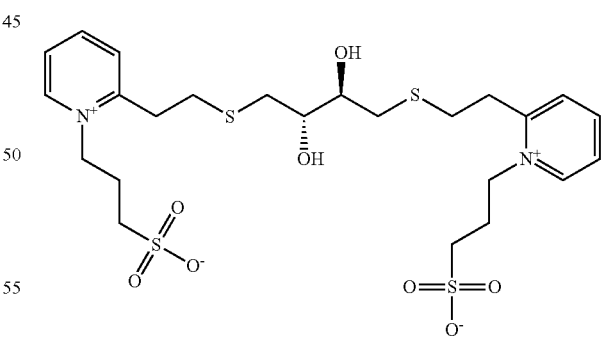

To a solution of 2.3 g 1-3(sulfopropyl)-2-vinylpyridinium hydroxide inner salt in 25 ml water was added 0.77 g dithioerythritol. After stirring 7 hours at reflux the reaction mixture was cooled to room temperature and stirred overnight. The reaction mixture was concentrated in vacuo, then methanol was added. The precipitated product was filtered off, washed with methanol and dried in vacuo to yield 1.8 g of 3-[2-[2-[(2S,3R)-2,3-dihydroxy-4-[2-[1-(3-sulfonatopropyl)pyridin-1-ium-2-yl]ethylsulfanyl]butyl]sulfanylethyl]

pyridin-1-ium-1-yl]propane-1-sulfonate as a white solid (mp. 195.2-198.5° C.°; assay by C-NMR 90-95%).

Example 1.31

3-[2-[2-[2-[2-[1-(3-Sulfonatopropyl)pyridine-1-ium-2-yl]ethylsulfanyl]ethylsulfanyl] ethyl]pyridine-1-ium-1-yl]propane-1-sulfonate

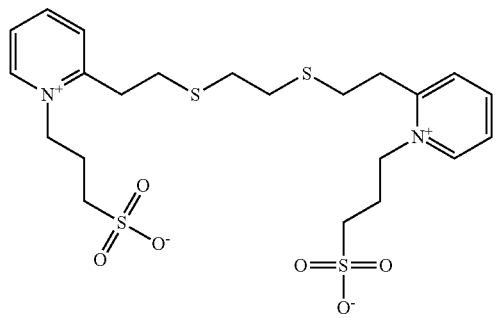 [SMILES: O=S(=O)([O-])CCC[n+]1ccccc1CCSCCSCCc1cccc[n+]1CCCS(=O)(=O)[O-]]

To a solution of 2,3 g 1-3(sulfopropyl)-2-vinylpyridinium hydroxide inner salt in 25 ml water was added 15 ml methanol and 420 µl 1,2-ethanedithiol. After stirring 7 hours at reflux the reaction mixture was cooled to room temperature and stirred overnight. The reaction mixture was concentrated in vacuo, then methanol was added. The precipitated product was filtered off, washed with methanol and dried in vacuo to yield 1.9 g of 3-[2-[2-[2-[2-[1-(3-sulfonatopropyl)pyridine-1-ium-2-yl]ethylsulfanyl]ethylsulfanyl]ethyl]pyridine-1-ium-1-yl]propane-1-sulfonate as a slightly yellowish solid (mp. 246.6-248.7° C.; assay by C-NMR 75-85%).

Example 1.32

1,3-Bis[3-[2-(2-pyridyl)ethylsulfanyl]propoxy]propane-2-ol

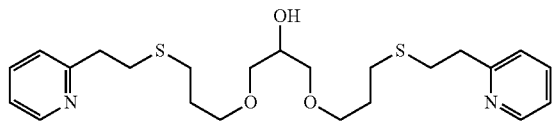 [SMILES: OC(COCCCSCCc1ccccn1)COCCCSCCc1ccccn1]

To a solution of 6.8 g 1,3-bis(3-sulfanylpropoxy)propane-2-ol in 30 ml iso-propanol was added 6.13 ml 2-vinylpyridine. After stirring 4 hours at reflux the reaction mixture was cooled to room temperature and stirred overnight. After concentration in vacuo the residue was purified by chromatography on silica gel with dichloromethane/methanol as the eluents (elution with a gradient) to yield 5 g of 1,3-bis[3-[2-(2-pyridyl)ethylsulfanyl]propoxy]propane-2-ol as a yellow oil (assay by C-NMR 95%).

Example 1.33

N1,N3-bis[2-[2-(2-Pyridyl)ethylsulfanyl]ethyl]benzene-1,3-dicarboxamide

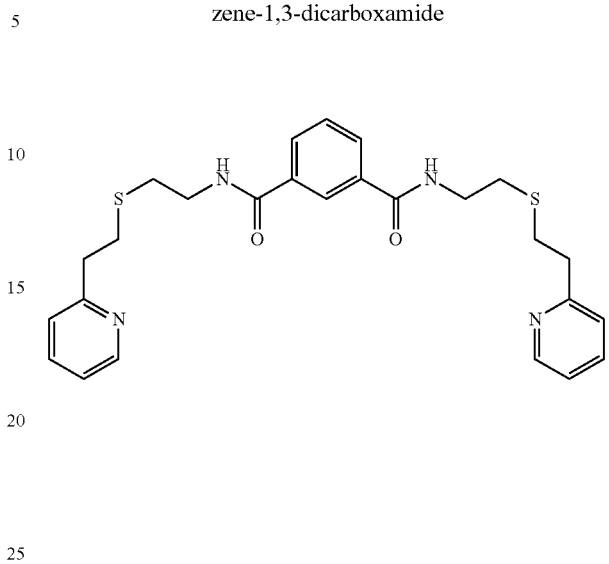

To a suspension of 2 g emeramide in 20 ml iso-propanol was added 1.54 ml 2-vinylpyridine. After stirring 7.5 hours at reflux the reaction mixture was cooled to room temperature and stirred overnight. After concentration in vacuo the residue was purified by chromatography on silica gel with dichloromethane/methanol as the eluents (elution with a gradient) to yield 2,6 g of N1,N3-bis[2-[2-(2-Pyridyl)ethylsulfanyl]ethyl]benzene-1,3-dicarboxamide as a light yellowish oil (assay by C-NMR>95%).

Example 1.34

2,3-Bis[2-(2-pyridyl)ethylsulfanyl]propane-1-sulfonate-sodium salt

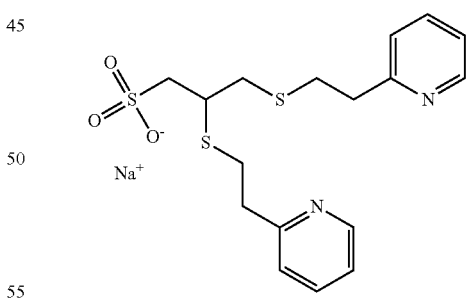

To a suspension of 1 g DL-2,3-dimercapto-1-propansulfonicacid-sodium salt monohydrate in 30 ml iso-propanol was added 911 µl 2-vinyl pyridine. After stirring 6 hours at reflux the reaction mixture was cooled to room temperature and stirred overnight. After concentration in vacuo the residue was purified by chromatography on silica gel with dichloromethane/methanol as the eluents (elution with a gradient) to yield 1.6 g of 2,3-Bis[2-(2-pyridyl)ethylsulfanyl]propane-1-sulfonate-sodium salt as a colorless oil (assay by C-NMR 90%).

Example 1.35

2-[2-[5-[2-(2-Pyridyl)ethylsulfanyl]pentylsulfanyl]ethyl]pyridine

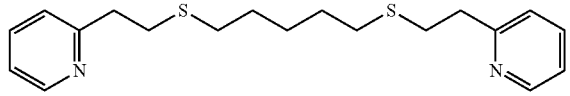 [SMILES: c1ccc(CCSCCCCCSCCc2ccccn2)nc1]

To a solution of 28.10 g 1,5-pentanedithiol in 100 ml iso-propanol was added 44.70 g 2-vinylpyridine at 84° C. After stirring 8 hours at reflux the reaction mixture was cooled to room temperature and stirred overnight. After concentration in vacuo the residue was purified by chromatography on silica gel with dichloromethane/methanol as the eluents (eluation with a gradient) to yield 57.6 g of 2-[2-[5-[2-(2-pyridyl)ethylsulfanyl]pentylsulfanyl]ethyl]pyridine as a yellow fluid (assay by C-NMR>95%).

Example 2

Stability Test

A silver methanesulfonic acid solution was added to the complexing agent (ratio complexing agent:Ag=10:1). If the complexing agent was insoluble, 2-3 drops of methanesulfonic acid were added. Next, a tin methanesulfonic acid solution containing 4-methoxyphenol (MeHQ) as antioxidant was added. The mixture was then stored at 50° C. for 7 days. If a precipitate was formed, the complexing agent failed the test. If the mixture stayed clear over a period of 3 days, this was an indication for a good complexation ("o"), if the mixture stayed clear over a period of 7 days for a very good complexation ("+").

Assumed that the reaction rate at temperatures <100° C. is tripled when the temperature is increased by 10° C., 7 days at 50° C. should reflect the stability of 6 months at 20° C.

The complexing agents of example 1 were subjected to the test procedure described above. The results are listed in Table 1.

TABLE 1

| No. 1.x | Struktur | Test Results |
|---|---|---|
| 1 | 1,8-Bis(2-pyridyl)-3,6-dithiaoctane | + |
| 2 | 1,9-Bis-(3-pyridyl)-2,5,8-trithianonane | + |
| 3 | 1,13-Bis(2-pyridyl)-2,5,9,12-tetrathiatridecane | + |
| 4 | (2R,3R)-1,4-bis[2-(2-pyridyl)ethylsulfanyl]butane-2,3-diol/(2S,3S)-1,4-bis[2-(2-pyridyl)-ethylsulfanyl]butane-2,3-diol | + |
| 5 | 1,6-Bis(2-methylpyridyl)-meso-dithioerythritol | o |
| 6 | 1,11-Bis(2-pyridyl)-6-oxa-3,9-dithiaundecane | + |
| 7 | 1,8-Bis(4-pyridyl)-3,6-dithiaoctane | + |
| 8 | 1,14-Bis(2-pyridyl)-6,9-dioxa-3,12-dithiatetradecane | + |
| 9 | 1,15-Bis(4-pyridyl)-3,6,10,13-tetrathiapentadecane | + |
| 10 | (2R,3S)-1,4-bis[2-(4-pyridyl)ethylsulfanyl]butane-2,3-diol | + |
| 11 | 1-[2-[2-(2-imidazol-1-ylethylsulfanyl)ethylsulfanyl]ethyl]imidazole | + |
| 12 | 1-methyl-2-[2-[2-[2-(1-methylpyridin-1-ium-2-yl)ethylsulfanyl]ethylsulfanyl]ethyl]pyridin-1-ium;methyl sulfate | o |
| 13 | 1,13-Bis(3-pyridyl)-2,5,9,12-tetrathiatridecane | + |
| 14 | 1,13-Bis(4-pyridyl)-2,5,9,12-tetrathiatridecane | + |
| 15 | 1-[3-[2-[2-(3-imidazol-1-ylpropylsulfanyl)ethylsulfanyl]-propyl]imidazole | + |
| 16 | (2S,3R)-1,4-bis(3-imidazol-1-ylpropylsulfanyl)butane-2,3-diol | + |
| 17 | (2R,3S)-1,4-bis(2-morpholinoethylsulfanyl)butane-2,3-diol | o |
| 18 | (2R,3S)-1,4-bis(2-imidazol-1-ylethylsulfanyl)butane-2,3-diol | + |
| 19 | 1-[2-[(2R,3S)-2,3-dihydroxy-4-[2-(2-oxopyrrolidin-1-yl)ethylsulfanyl]butyl]sulfanylethyl]pyrrolidin-2-one | + |
| 20 | 2,2-bis[3-[2-(2-pyridyl)ethylsulfanyl]propoxymethyl]butan-1-ol | + |
| 21 | 1-[2-[2-[2-(2-imidazol-1-ylethylsulfanyl)ethylsulfanyl]ethylsulfanyl]ethyl]imidazole | + |
| 22 | 1,10-Bis(2-pyridyl)-3,8-dithiadecane | + |
| 23 | (2R,3S)-1,4-bis(2-pyrazin-2-ylethylsulfanyl)butane-2,3-diol | o |
| 24 | (2R,3S)-1,4-bis(2-thiazol-2-ylpropylsulfanyl)butane-2,3-diol | + |
| 25 | 3-[2-(2-pyridyl)ethyl]-5-[2-(2-pyridyl)ethylsulfanyl]-1,3,4-thiadiazole-2-thione | + |
| 26 | 2,3-bis[2-(2-pyridyl)ethylsulfanyl]propan-1-ol | + |
| 27 | 6,8-bis[2-(2-pyridyl)ethylsulfanyl]octanoic acid | + |
| 28 | 2-[2-[[5-[2-(2-pyridyl)ethylsulfanylmethyl]-1,4-dithian-2-yl]methylsulfanyl]ethyl]pyridine | + |
| 29 | 4,6-bis[2-(2-pyridyl)ethylsulfanyl]-1,3,5-triazin-2-amine | + |
| 30 | 3-[2-[2-[(2S,3R)-2,3-dihydroxy-4-[2-[1-(3-sulfonatopropyl)pyridine-1-ium-2-yl]ethylsulfanyl]butyl]sulfanylethyl]pyridine-1-ium-1-yl]propane-1-sulfonate | + |
| 31 | 3-[2-[2-[2-[2-[1-(3-Sulfonatopropyl)pyridine-1-ium-2-yl]ethylsulfanyl]ethylsulfanyl]ethyl]pyridine-1-ium-1-yl]propane-1-sulfonate | + |

TABLE 1-continued

| No. 1.x | Struktur | Test Results |
|---|---|---|
| 32 | 1,3-Bis[3-[2-(2-pyridyl)ethylsulfanyl]propoxy]propane-2-ol | o |
| 33 | N1,N3-bis[2-[2-(2-Pyridyl)ethylsulfanyl]ethyl]benzene-1,3-dicarboxamide | + |
| 34 | 2,3-Bis[2-(2-pyridyl)ethylsulfanyl]propane-1-sulfonate-sodium salt | + |
| 35 | 2-[2-[5-[2-(2-Pyridyl)ethylsulfanyl]pentylsulfanyl]ethyl]pyridine | + |

The invention claimed is:

1. An aqueous composition, comprising:
 (a) metal ions comprising tin ions and silver ions; and
 (b) a complexing agent of formula C1, C2, and/or C3

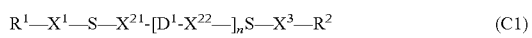  (C1)

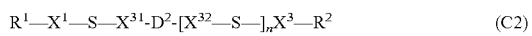  (C2)

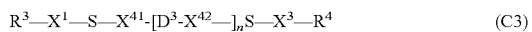  (C3)

wherein
$X^1$, $X^3$, $X^{41}$, $X^{42}$ are independently C1-C12 alkanediyl, optionally substituted by OH;
$X^{21}$, $X^{22}$ are independently
(i) $X^1$, optionally further substituted by —$X^5$—$COOR^{12}$, —$X^5$—$SO_2$—O—$R^{12}$, and/or a $C_2$ to $C_6$ polyoxyalkylene group of formula —(O—$CH_2$—$CHR^{11}$)$_z$—OH, and
(ii) —$X^1$—NH—CO—$X^6$—CO—NH—$X^1$—;
$X^{31}$, $X^{32}$ are independently a chemical bond or $X^1$;
$X^5$ is $C_1$ to $C_{10}$ alkyl;
$X^6$ is $X^1$ or a divalent 5 or 6 membered aromatic group;
$R^1$, $R^2$ are independently a monovalent 5 or 6 membered aromatic N-heterocyclic group comprising one or two N atoms which are separated by at least one C atom, or a derivative of N-heterocyclic group by N-alkylation with a $C_1$-$C_6$-alkyl group, optionally substituted by —$COOR^{12}$ or —$SO_2$—O—$R^{12}$, the aromatic N-heterocyclic group optionally further comprising, when $X^{21}$ is substituted by at least one OH, one S atom;
$R^3$, $R^4$ are independently a monovalent 5 or 6 membered aliphatic N-heterocyclic group comprising one N atom and one O atom;
$D^1$ is independently S, O, or $NR^{10}$;
$D^2$ is (i) a divalent 5 or 6 membered aliphatic heterocyclic ring system comprising 1 or 2 S atoms, or (ii) a 5 or 6 membered aromatic heterocyclic ring system comprising at least two N atoms and optionally one or two S atoms;
$D^3$ is independently S or $NR^{10}$;
n is an integer in a range of from 0 to 5;
z is an integer in a range of from 1 to 50;
$R^{10}$ is H or $C_1$-$C_{12}$ alkyl;
$R^{11}$ is H or $C_1$ to $C_6$ alkyl; and
$R^{12}$ is $R^{10}$ or a cation.

2. The composition of claim 1, wherein $X^1$ and $X^3$ are $C_1$-$C_8$ alkanediyl optionally substituted by OH.

3. The composition of claim 1, wherein $R^1$ and $R^2$ are independently N-imidazole, N-pyrazol, 2-thiazole, 2-pyridine, 3-pyridine, 4-pyridine, or 2-pyrazine.

4. The composition of claim 1, wherein $R^3$ and $R^4$ are independently N-pyrrolidone or N-morpholine.

5. The composition of claim 1, wherein n is 0 or an integer in a range of from 1 to 3.

6. The composition of claim 1, wherein $D^1$ is S or O.

7. The composition of claim 1, wherein $D^2$ is
(i) a 5-membered aliphatic heterocyclic ring system having 2 S atoms or 1 S and 1 N atom, or
(ii) a 6-membered aliphatic heterocyclic ring system having 2 S atoms or 1 S and 1 N atom.

8. The composition of claim 1, wherein $D^3$ is S.

9. The composition of claim 1, wherein the complexing agent has the formula $C_1$, wherein $X^{21}$ and $X^{22}$ are independently $C_1$-$C_8$ alkanediyl optionally substituted by OH, $X^5$—$COOR^{12}$, or —$SO_2$—$OR^{12}$.

10. The composition of claim 1, wherein $X^{31}$ and $X^{32}$ are independently $C_1$-$C_8$ alkanediyl, optionally substituted by OH.

11. The composition of claim 1, wherein $X^{41}$ and $X^{42}$ are independently a $C_1$-$C_8$ alkanediyl, optionally substituted by OH.

12. The composition of claim 1, comprising no grain refiner.

13. The composition of claim 1, comprising no copper.

14. The composition of claim 1, wherein the metal ions consist of tin ions and silver ions.

15. A substrate, comprising:
features having an aperture size in a range of from 500 nm to 500 μm; and
a deposition on the substrate made from the composition of claim 1.

16. A process for electrodepositing tin or a tin silver alloy onto a substrate, the process comprising:
a) contacting the composition of claim 1 with the substrate; and
b) applying a current to the substrate for a time sufficient to deposit a tin or tin alloy layer onto the substrate,
wherein the substrate comprises features having an aperture size in a range of from 500 nm to 500 μm and the deposition is performed to fill these features.

17. The process of claim 16, wherein the aperture size is in a range of from 1 μm to 200 μm.

18. A compound of formula C1, C2, or C3

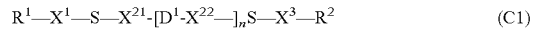  (C1)

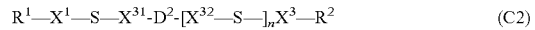  (C2)

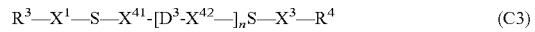  (C3)

wherein
$X^1$, $X^3$, $X^{41}$, $X^{42}$ are independently a $C_1$-$C_{12}$ alkanediyl, optionally substituted by OH;
$X^{21}$, $X^{22}$ are independently
(i) $X^1$, optionally further substituted by —$X^5$—$COOR^{12}$, —$X^5$—$SO_2$—O—$R^{12}$, and/or a $C_2$ to $C_6$ polyoxyalkylene group of formula —(O—$CH_2$—$CHR^{11}$)$_z$—OH, or (ii) —$X^1$—NH—CO—$X^6$—CO—NH—$X^1$—;
$X^{31}$, $X^{32}$ are independently a chemical bond or $X^1$,
$X^5$ is a $C_1$ to $C_{10}$ alkyl;
$X^6$ is $X^1$ or a divalent 5 or 6 membered aromatic group;

$R^1$, $R^2$ are independently a monovalent 5 or 6 membered aromatic N-heterocyclic group comprising one or two N atoms which are separated by at least one C atom, or a derivative of the N-heterocyclic group by N-alkylation with a $C_1$-$C_6$-alkyl group, optionally substituted by —$COOR^{12}$ or —$SO_2$—O—$R^{12}$, the aromatic N-heterocyclic group optionally further comprising, when $X^{21}$ is substituted by at least one OH, one S atom;

$R^3$, $R^4$ are independently a monovalent 5 or 6 membered aliphatic N-heterocyclic group comprising one N atom and one O atom;

$D^1$ is independently S, O, or $NR^{10}$, $D^2$ is (i) a divalent 5 or 6 membered aliphatic heterocyclic ring system comprising 1 or 2 S atoms, or (ii) a 5 or 6 membered aromatic heterocyclic ring system comprising at least two N atoms and optionally one or two S atoms;

$D^3$ is independently S or $NR^{10}$, n is an integer in a range of from 0 to 5;

z is an integer in a range of from 1 to 50;

$R^{10}$ is H or $C_1$-$C_{12}$ alkyl;

$R^{11}$ is H or $C_1$ to $C_6$ alkyl; and $R^{12}$ is $R^{10}$ or a cation;

excluding 1,8-bis(2-pyridyl)-3,6-dithiaoctane; 1,9-bis-(2-pyridyl)-2,5,8-trithianonane;

1,11-bis(2-pyridyl)-3,6,9-trithiaundecane; 1,6-bis(2-pyridyl)-2,5-dithiahexane; 1,13-bis(2-pyridyl)-2,5,9,12-tetrathiatridecane; 1,9-bis(2-pyridyl)-5-oxa-2,8-dithianonane; 1,8-bis(4-pyridyl)-3,6-dithiaoctane; 1-[2-[2-(2-imidazol-1-ylethylsulfanyl)ethylsulfanyl]ethyl]imidazole;

1-[2-[2-[2-(2-imidazol-1-ylethylsulfanyl)ethylsulfanyl]ethylsulfanyl]ethyl]imidazole; 1,9-bis(2-pyridyl)-3,7-dithianonane; and 1,10-bis(2-pyridyl)-3,8-dithiadecane;

wherein:

(a) if n is 0, $X^{21}$ is substituted by at least one OH; and (b) if n is 1, $D^1$ is O or $NR^{10}$ and, if $X^1$ and $X^3$ are methanediyl, at least one of $R^1$ and $R^2$ is not 2-pyridiyl; or (c) if n is greater than 1, $D^1$ is O or $NR^{10}$.

19. The compound of claim 18 comprising, optionally as a salt, 1,9-bis-(3-pyridyl)-2,5,8-trithianonane; 1,15-bis(2-pyridyl)-3,6,10,13-tetrathiapentadecane; (2R,3R)-1,4-bis[2-(2-pyridyl)ethylsulfanyl]butane-2,3-diol; (2S,3S)-1,4-bis[2-(2-pyridyl)-ethylsulfanyl]butane-2,3-diol; (2R,3S)-1,4-bis[2-(2-pyridyl)ethylsulfanyl]butane-2,3-diol; 1,9-bis-(3-pyridyl)-2,5,8-trithianonane; 1,15-bis(2-pyridyl)-3,6,10,13-tetrathiapentadecane; (2R,3R)-1,4-bis[2-(2-pyridyl)ethylsulfanyl]butane-2,3-diol; (2S,3S)-1,4-bis[2-(2-pyridyl)-ethylsulfanyl]butane-2,3-diol; (2R,3S)-1,4-bis[2-(2-pyridyl)-ethylsulfanyl]butane-2,3-diol; 1,6-bis(2-methylpyridyl)-DL-dithiothreitol; 1,6-bis(2-methylpyridyl)-meso-dithioerythritol; 1,11-bis(2-pyridyl)-6-oxa-3,9-dithiaundecane; 1,14-bis(2-pyridyl)-6,9-dioxa-3,12-dithiatetradecane; 1,11-bis(4-pyridyl)-6-oxa-3,9-dithiaundecane; 1,14-bis(4-pyridyl)-6,9-dioxa-3,12-dithiatetradecane; 1,11-bis(4-pyridyl)-3,6,9-trithiaundecane;

1,15-bis(4-pyridyl)-3,6,10,13-tetrathiapentadecane; (2R,3S)-1,4-bis[2-(4-pyridyl)ethylsulfanyl]butane-2,3-diol; 1-methyl-2-[2-[2-[2-(1-methylpyridin-1-ium-2-yl)-ethylsulfanyl]ethylsulfanyl]ethyl]pyridin-1-ium methylsulfate; 1,13-bis(3-pyridyl)-2,5,9,12-tetrathiatridecane; 1,9-bis-(4-pyridyl)-2,5,8-trithianonane; 1,13-bis(4-pyridyl)-2,5,9,12-tetrathiatridecane, 1-[3-[2-[2-(3-imidazol-1-ylpropylsulfanyl)ethylsulfanyl]ethylsulfanyl]propyl]imidazole; 1,9-bis(4-pyridyl)-5-oxa-2,8-dithianonane; (2S,3R)-1,4-bis(3-imidazol-1-ylpropylsulfanyl)butane-2,3-diol, (2R,3S)-1,4-bis(2-morpholinoethylsulfanyl)butane-2,3-diol; 4-[2-[2-[2-(4-pyridylmethylsulfanyl)ethoxy]ethoxy] ethylsulfanylmethyl]pyridine; (2R,3S)-1,4-bis(2-imidazol-1-ylethylsulfanyl)butane-2,3-diol; 1-[2-[(2R,3S)-2,3-dihydroxy-4-[2-(2-oxopyrrolidin-1-yl) ethylsulfanyl]butyl]sulfanylethyl]-pyrrolidin-2-one; 2,2-bis[3-[2-(2-pyridyl)ethylsulfanyl]propoxymethyl] butan-1-ol; 1-[2-[2-[2-[2-(2-oxopyrrolidin-1-yl)ethylsulfanyl]ethylsulfanyl]ethylsulfanyl]ethyl]pyrrolidin-2-one; (2R,3S)-1,4-bis(2-pyrazin-2-ylethylsulfanyl) butane-2,3-diol; (2S,3S)-1,4-bis[2-(4-pyridyl) ethylsulfanyl]butane-2,3-diol; (2R,3R)-1,4-bis[2-(4-pyridyl)ethylsulfanyl]butane-2,3-diol; 3-[2-(2-pyridyl) ethyl]-5-[2-(2-pyridyl)ethylsulfanyl]-1,3,4-thiadiazole-2-thione; 2,3-bis[2-(2-pyridyl)ethylsulfanyl]propan-1-ol; 6,8-bis[2-(2-pyridyl)ethylsulfanyl]octanoic acid; 2-[2-[[5-[2-(2-pyridyl)ethylsulfanylmethyl]-1,4-dithian-2-yl]methylsulfanyl]ethyl]pyridine; 4,6-bis[2-(2-pyridyl)ethylsulfanyl]-1,3,5-triazin-2-amine; (2R,3S)-1,4-bis(2-thiazol-2-ylpropylsulfanyl)-butane-2,3-diol; 3-[2-[2-[(2S,3R)-2,3-dihydroxy-4-[2-[1-(3-sulfonatopropyl)pyridine-1-ium-2-yl]ethylsulfanyl] butyl]sulfanylethyl]pyridine-1-ium-1-yl]propane-1-sulfonate;
3-[2-[2-[2-[2-[1-(3-sulfonatopropyl)pyridine-1-ium-2-yl]ethylsulfanyl]ethylsulfanyl]ethyl]pyridine-1-ium-1-yl]propane-1-sulfonate; 1,3-bis[3-[2-(2-pyridyl)ethylsulfanyl]propoxy]propane-2-ol; N1,N3-bis[2-[2-(2-pyridyl)ethylsulfanyl]ethyl]benzene-1,3-dicarboxamide; 2,3-bis[2-(2-pyridyl)ethyl-sulfanyl] propane-1-sulfonate; and/or 2-[2-[5-[2-(2-pyridyl) ethylsulfanyl]pentylsulfanyl]-ethyl]pyridine.

* * * * *